(12) United States Patent
Iqbal et al.

(10) Patent No.: US 8,796,214 B2
(45) Date of Patent: *Aug. 5, 2014

(54) NEUROTROPHIC PEPTIDES

(71) Applicant: The Research Foundation for Mental Hygiene, Inc., Menands, NY (US)

(72) Inventors: Khalid Iqbal, Staten Island, NY (US); Inge Grundke-Iqbal, Staten Island, NY (US)

(73) Assignee: Research Foundation For Mental Hygiene, Inc., Menands, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/674,556

(22) Filed: Nov. 12, 2012

(65) Prior Publication Data

US 2013/0143809 A1 Jun. 6, 2013

Related U.S. Application Data

(63) Continuation-in-part of application No. 13/044,323, filed on Mar. 9, 2011, which is a continuation-in-part of application No. 12/531,616, filed as application No. PCT/EP2008/002106 on Mar. 17, 2008, now Pat. No. 8,338,378.

(30) Foreign Application Priority Data

Mar. 16, 2007 (EP) ..................................... 07450050

(51) Int. Cl.
*A01N 37/18* (2006.01)
*A61K 38/00* (2006.01)

(52) U.S. Cl.
USPC ........... 514/17.7; 514/8.3; 514/8.4; 514/17.5; 514/21.6; 514/21.9

(58) Field of Classification Search
None
See application file for complete search history.

(56) References Cited

U.S. PATENT DOCUMENTS 6,472,178 B1 * 10/2002 Fandl et al. .................. 435/69.4
8,338,378 B2 * 12/2012 Mossler et al. .............. 514/17.7

* cited by examiner

*Primary Examiner* — Olga N Chernyshev
(74) *Attorney, Agent, or Firm* — David L. Nocilly; Bond Schoeneck & King, PLLC

(57) ABSTRACT

The present invention relates to a neurotrophic peptide having an amino acid sequence of VGDGGLFEKKL (SEQ ID NO:1) and alternatively comprising an adamantyl group at the C- and/or N-terminal end. The neurotrophic peptide can rescue cognition, correct impairments in neural cell proliferation and synaptic plasticity, and thus address the cognitive defects associated with Down syndrome.

8 Claims, 15 Drawing Sheets

(a)

(b)

NEUROTROPHIC PEPTIDES

CROSS-REFERENCE TO RELATED APPLICATIONS

The present application is a continuation-in-part of Ser. No. 13/044,323, filed on Mar. 9, 2011, which is a continuation-in-part of U.S. patent application Ser. No. 12/531,616 filed Sep. 16, 2009, which is a national stage application of PCT/EP2008/002106, filed on Mar. 17, 2008, which claims priority to European Application No. 07450050.5 filed Mar. 16, 2007, all of which are hereby incorporated by reference in their entireties.

BACKGROUND OF THE INVENTION

1. Field of the Invention

The present invention relates to neurotrophic and/or neurogenic peptides and their use for manufacturing a medicament for the treatment of neurodegenerative diseases.

2. Description of the Related Art

The population in the industrialised countries is rapidly ageing due to a greater life expectancy, and an ever-increasing number of people are afflicted with neurodegenerative diseases making a global issue out of these diseases.

Neurodegenerative diseases result from the gradual and progressive loss of neural cells, leading to nervous system dysfunction, and may have next to ageing various causes (e.g. environmental influences, genetic defects). Until now, more than 600 neurologic disorders are known.

The major known risk factors for neurodegenerative disease include certain genetic polymorphisms and increasing age. Other possible causes may include gender, poor education, endocrine conditions, oxidative stress, inflammation, stroke, hypertension, diabetes, smoking, head trauma, depression, infection, tumors, vitamin deficiencies, immune and metabolic conditions, and chemical exposure. Because the pathogenesis of many of these diseases remains unknown, also the role of environmental factors in these diseases may be considered. An overview of neurodegenerative diseases can be found, for instance, in "Neurodegenerative Diseases: Neurobiology, Pathogenesis and Therapeutics" (M. Flint Beal, Anthony E. Lang, and Albert C. Ludolph; Cambridge University Press; 2005).

In order to treat neurodegenerative diseases several medicaments comprising one or more active compounds like Piracetam, Nimotop, Vinpocetin, Gliatilin, Cerebrolysin, Cytoflavin etc. are regularly employed. The compounds known in the art have varying modes of action. Cerebrolysin, for instance, a peptide based drug produced from purified animal brain proteins by standardized enzymatic breakdown, is exerting nerve growth factor like activity on neurons from dorsal root ganglia, neurotrophic and neuroprotective effects.

US 2004/102370 relates to peptides comprising the essential tetrameric peptide structural unit Xaa-Xaa-Xaa-Xaa (SEQ. ID. NO. 14) in which Xaa at position 1 represents Glu or Asp, Xaa at position 2 represents any amino acid, Xaa at position 3 represents any amino acid and Xaa at position 4 represents Glu or Asp. Said peptides are used to treat neurodegenerative diseases and nerve damages, and are described to be stimulators of axonal regeneration and survival.

Ciliary neurotrophic factor (CNTF) is a survival factor for various neuronal cell types. The human CNTF protein comprises 200 amino acid residues and shares significant sequence homology with CNTF proteins from other mammalian sources. The gene for human CNTF has been cloned and recombinant forms of the protein are available for clinical trials in humans (WO 91/04316). Over the past decade, a number of biological effects have been ascribed to CNTF in addition to its ability to support the survival of ciliary ganglion neurons. CNTF is believed to induce the differentiation of bipotential glial progenitor cells in the perinatal rat optic nerve and brain (Hughes et al., 1988, Nature 335:70-73). Furthermore, it has been observed to promote the survival of embryonic chick dorsal root ganglion sensory neurons (Skaper and Varon, 1986, Brain Res. 389:39-46). In addition, CNTF supports the survival and differentiation of motor neurons, hippocampal neurons and presympathetic spinal cord neurons (Sendtner, et al., 1990, Nature 345: 440-441).

In addition to human CNTF, the corresponding rat and rabbit genes have been cloned and found to encode a protein of 200 amino acids, which share about 80% sequence identity with the human gene.

Despite their structural and functional similarity, recombinant human and rat CNTF differ in several respects. The biological activity of recombinant rat CNTF in supporting survival and neurite outgrowth from embryonic chick ciliary neurons in culture is four times better than that of recombinant human CNTF (Masiakowski et al., 1991, J. Neurochem. 57:1003-1012). Further, rat CNTF has a higher affinity for the human CNTF receptor than does human CNTF.

As described in WO 99/43813 one of the uses of CNTF is the use of CNTF for the treatment of Huntington's disease. Huntington's disease (HD) is a hereditary degenerative disorder of the central nervous system.

However, the administration of CNTF to the human body has several drawbacks. While its therapeutic potential for CNS diseases is well recognized, the blood brain barrier (BBB) hinders the systemic delivery of CNTF and direct bolus injections are not suitable due to the short half-life of CNTF. One method of overcoming the blood brain barrier while providing continuous delivery of CNTF is, e.g., with immunoisolated cellular implants that produce and deliver CNTF directly to the region of interest. Cells can be protected from host rejection by encapsulating, or surrounding, them within an immunoisolatory, semipermeable membrane that admits oxygen and required nutrients and releases bioactive cell secretions, but restricts passage of larger cytotoxic agents from the host immune defense system. The selective membrane eliminates the need for chronic immunosuppression of the host and allows the implanted cells to be obtained from nonhuman sources. However, also this method is not advantageous.

Down syndrome (DS) is caused by a triplication of human chromosome 21 and results in moderate to profound intellectual disability (1, 2). Individuals with DS have abnormalities in learning, memory, and language and mental retardation that is essentially universal (3). Postnatally, the DS brain exhibits degeneration of cortical neurons (4), profound dendritic and synaptic abnormalities (5-8), and a hypocellular hippocampus and cerebral cortex (9, 10). Changes in dendritic structure, branching and spine counts, particularly in the hippocampus (11), seem to contribute substantially to cognitive dysfunction in DS (12).

The most widely used animal model of DS, the Ts65Dn mouse, is segmentally trisomic for chromosome 16 and carries 3 copies of genes orthologous to those of human chromosome 21 (13, 14). Ts65Dn mice exhibit several features characteristic of DS, including cognitive impairment (15-19), alterations in the structure of dendritic spines in cortex and hippocampus (20), and failed long-term potentiation in the hippocampus and fascia dentata (21-23). In addition, several studies reported severe impairment of neuronal proliferation in the dentate gyrus of neonate and adult Ts65Dn mice.

Accordingly, there is a need for a treatment that optimizes the microenvironment for neuronal proliferation and synaptic plasticity in the brain to restore the homeostasis of the brain biochemical milieu.

BRIEF SUMMARY OF THE INVENTION

It is therefore a principal object and advantage of the present invention to provide new medicaments comprising substances which have substantially the same or even better neurotrophic and/or neurogenic effects than CNTF. Advantageously these substances should also be able to pass the blood brain barrier in order to reach the wanted site of action in the brain.

In accordance with the foregoing objects and advantages, the present invention provides a neurotrophic and/or neurogenic peptide having an amino acid sequence selected from the group consisting of VGDGGLFEKKL (SEQ ID No. 1), EDQQVHFTPTEG (SEQ ID No. 2) or IPENEADGMPATV (SEQ ID No. 3).

It has surprisingly been found that the peptides of the present invention, which are derivable from rat or human CNTF, show neurotrophic and/or neurogenic (causing growth of nerve tissue) effects which are comparable to the wild-type CNTF. Furthermore due to their small size these peptides are also able to pass the blood brain barrier.

Fragments of SEQ ID No. 1 to 3 preferably comprise 4 to 10, more preferably 4 to 8, even more preferably 4 to 6, amino acids and include:

| Source | Sequence | SEQ ID No. |
|---|---|---|
| SEQ ID No. 1 | GDGGLFEK | 5 |
| | GLFEKKLW | 6 |
| | VGDG | 7 |
| | GDGG | 8 |
| | DGGL | 9 |
| | GGLF | 10 |

The peptides of the present invention and their fragments may be fused to other proteins, polypeptides or peptides (N- or C-terminally), or conjugated to other substances. The resulting fusions may also comprise more than one peptide of the present invention (e.g. SEQ ID No. 1 may be fused to SEQ ID No. 2). The peptides of these polypeptides may be fused directly or via a linker to each other. Therefore, the present invention also relates to a polypeptide comprising at least two, preferably at least three, peptides of the present invention (SEQ ID No. 1 to 10).

The peptides of the present invention may also be bound or conjugated to substances which enhance their ability to pass through the blood brain barrier.

"Fragments", as used herein, refer to parts of the peptides of the present invention, which are directly derivable from said peptides and show the same as or enhanced neurotrophic and neurogenic activities than the wild-type CNTF.

According to the present invention also peptides are encompassed which exhibit at least 80%, preferably 90%, more preferably 95%, identity with the peptides of the present invention selected from the group consisting of SEQ ID No. 1 to 3.

According to the present invention "identity" ("identical") is determined by comparing two optimally aligned sequences over a comparison window, where the fragment of the amino acid sequence in the comparison window may comprise additions or deletions (e.g., gaps or overhangs) as compared to the reference sequence (which does not comprise additions or deletions) for optimal alignment of the two sequences. In general, sequences are aligned so that the highest order match is obtained (see, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; Carillo et al. (1988) SIAM J Applied Math 48:1073).

Whether any two amino acid molecules have amino sequences that are at least, for example, 80%, 85%, 90%, 95%, 96%, 97%, 98% or 99% "identical", can be determined using known computer algorithms such as the "FAST A" program, using for example, the default parameters as in Pearson et al. (1988) PNAS USA 85: 2444 (other programs include the GCG program package (Devereux, J., et al., Nucleic Acids Research (1984) Nucleic Acids Res., 12, 387-395), BLASTP, BLASTN, FASTA (Atschul, S. F., et al., J Molec Biol 215: 403 (1990); Guide to Huge Computers, Martin J. Bishop, ed., Academic Press, San Diego, 1994, and Carillo et al, (1988) SIAM J Applied Math 48: 1073). For instance, the BLAST tool of the NCBI database can be used to determine identity. Other commercially or publicly available programs include, DNAStar "MegAlign" program (Madison, Wis.) and the University of Wisconsin Genetics Computer Group (UWG) "Gap" program (Madison, Wis.). Percent identity of proteins and/or peptides can be determined, for example, by comparing sequence information using a GAP computer program (e.g. Needleman et al., (1970) J. Mol. Biol. 48:443, as revised by Smith and Waterman (1981) Adv. Appl. Math. 2:482). Briefly, the GAP program defines similarity as the number of aligned symbols (i.e., nucleotides or amino acids) which are similar, divided by the total number of symbols in the shorter of the two sequences. Default parameters for the GAP program can include: (1) a unary comparison matrix (containing a value of 1 for identities and for non-identities) and the weighted comparison matrix of Gribskov et al. 14:6745, as described by Schwartz and Dayhoff, eds., ATLAS OF PROTEIN SEQUENCE AND STRUCTURE, National Biomedical Research Foundation, pp. 353-358 (1979); (2) a penalty of 3.0 for each gap and an additional 0.10 penalty for each symbol in each gap; and (3) no penalty for end gaps.

As used herein, the term "at least 80% identical to" refers to percent identities from 80 to 99.99 relative to the reference peptides. Consequently, the peptides of the present invention may also comprise one or more amino acid modifications (i.e. substitutions, deletions, insertions) provided that the peptides still exhibit neurotrophic and/or neurogenic activity.

Identity at a level of 80% or more is indicative of the fact that, assuming for exemplification purposes a test and reference polypeptide length of 100 amino acids is compared, no more than 20% (i.e. 20 out of 100) of amino acid residues in the test polypeptide differs from that of the reference polypeptide. Such differences can be represented as point mutations randomly distributed over the entire length of an amino acid sequence or they can be clustered in one or more locations of varying length up to the maximum allowable, e.g. 20/100 amino acid difference (approx. 80% identity). Differences are defined as amino acid substitutions, insertions or deletions. At the level of homologies or identities above about 85-90%, the result should be independent of the program and gap parameters set; such high levels of identity can be assessed readily, often without relying on software.

According to a preferred embodiment of the present invention the neurotrophic peptide of the present invention is identical to SEQ ID No. 1, 2 or 3, which means that the neurotrophic peptide consists of said amino acids sequences or fragments thereof. Of course, the peptide of the present invention may comprise modifications such as substitution of L-amino acids with D-amino acids, introduction of hydrophobic side chains, modifications allowing the formation of dimers (or even multimers) or cyclic peptide variants. The respective methods are well known in the art.

The peptide according to the present invention is preferably non immunogenic. The term "non immunogenic peptide" as used herein refers to a molecule, in particular to a peptide, which does substantially not provoke an immune response in vivo when administered to a human or an animal being. This molecule property can be determined by methods known in the art. For instance, if the administration of a molecule according to the present invention to an animal (e.g. rabbit, mouse) provokes in an animal a substantial increase of antibodies directed against said molecule, said molecule is considered as an "immunogenic peptide", if, however, substantially no molecule-specific antibodies can be induced in an animal or human upon administration of said molecule, it is considered as a "non immunogenic peptide". It is important that the peptides according to the present invention are non immunogenic because immunogenic peptides are normally eliminated from the body by the immune system.

The basic structure of the peptide according to the present invention, which is formed by amino acids, is preferably synthesised chemically according to methods known in the art, e.g. by the method developed by Merrifield et al. (Merrifield, R. B. (1963) J. Am. Chem. Soc. 85, 2149-2154; solid phase peptide synthesis).

The solid phase peptide synthesis method introduced by Merrifield in 1963, for instance, involves the attachment of a growing peptide chain to a solid support. An amino acid corresponding to the C-terminal of the target peptide is covalently attached to an insoluble polymeric support (the "resin"). The next amino acid, with a protected alpha-amino acid, is activated and reacted with the resin-bound amino acid to yield an amino-protected dipeptide on the resin. The amino-protecting group is removed and chain extension is continued with the third and subsequent protected amino acids. After the target protected peptide chain has been built up the resin is cleaved by suitable chemical means thereby releasing the crude peptide product into solution (for solid phase peptide synthesis methods and other peptide synthesis methods see also Fields, G. B. (ed.), Solid Phase Peptide Synthesis in Methods in ENZYMOLOGY, Vol. 289, Academic Press, San Diego (1997); Bodansky, M., Bodansky, A., The practice of peptide synthesis (2nd edn.), Springer Verlag, Berlin (1995); Pennington, M. W., Dunn, B. M. (eds), Peptide Synthesis Protocols, in Methods in Molecular Biology, Vol. 35, Humana Press Inc., Totowa (1994); Grant, G. A. (ed.), Synthetic peptides: a user's guide, W. H. Freemann & Co., New York (1992)).

The inorganic cation at the C-terminal end of the peptide according to the present invention may be an alkali metal or alkali earth metal cation, preferably a lithium, sodium, potassium, magnesium or calcium cation.

These inorganic cations are regularly used to prepare salts of pharmaceutically active substances.

The organic cation may be a quaternary ammonium ion.

If the N-terminal end of the peptide according to the present invention comprises a positive charge, said charge may be preferably compensated by an equivalent of an inorganic or organic anion. The organic anion can be, for instance, acetate anion.

Of course it is also possible to use molecules, preferably small molecules, mimicking the peptides of the present invention.

Another aspect of the present invention relates to a pharmaceutical composition comprising at least one peptide according to the present invention and/or at least one peptide having an amino acid sequence selected from the group consisting of GDGGLFEK (SEQ ID No. 5), GLFEKKLW (SEQ ID No. 6), VGDG (SEQ ID No. 7), GDGG (SEQ ID No. 8), DGGL (SEQ ID No. 9) and GGLF (SEQ ID No. 10) and optionally at least one pharmaceutically acceptable excipient and/or carrier.

The peptide according to the present invention may be formulated in a pharmaceutical preparation, which can be administered to a patient for preventing or treating a cerebral disease, in particular a neurodegenerative disease. The pharmaceutical preparation may further comprise pharmaceutically acceptable excipients and/or carriers. Suitable excipients and carriers are well known in the art (see e.g. "Handbook of Pharmaceutical Excipients", 5th Edition by Raymond C. Rowe, Paul J. Sheskey, Sian C. Owen (2005), APhA Publications).

The composition of the present invention may further comprise at least one additional pharmaceutically active component, which is preferably IPRNEADGMPINV (SEQ ID No. 4).

The pharmaceutical preparation according to the present invention may comprise next to the peptide according to the present invention further active components, which may exhibit similar properties when administered to an individual or which may cause other reactions in the treated patient.

According to the present invention, e.g., antioxidants like vitamins may be considered as further active components because antioxidants inhibit oxidation or suppress reactions promoted by oxygen, oxygen free radicals, oxygen reactive species including peroxides. Antioxidants, especially lipid-soluble antioxidants, can be absorbed into the cell membrane to neutralize oxygen radicals and thereby protect the membrane. The antioxidants useful in the present invention are preferably vitamin antioxidants that may be selected from the group consisting of all forms of Vitamin A including retinal and 3,4-didehydroretinal, all forms of carotene such as alpha-carotene, beta-carotene, gamma carotene, delta-carotene, all forms of Vitamin C (D-ascorbic acid, L-ascorbic acid), all forms of tocopherol such as Vitamin E (Alpha-tocopherol, 3,4-dihydro-2,5,7,8-tetramethyl-2-(4,8,12-trimethyltri-decyl)-2H-1-benzopyran-6-01), beta-tocopherol, gamma-tocopherol, delta-tocopherol, tocoquinone, tocotrienol and Vitamin E esters which readily undergo hydrolysis to Vitamin E such as Vitamin E acetate and Vitamin E succinate, and pharmaceutically acceptable Vitamin E salts such as Vitamin E phosphate, prodrugs of Vitamin A, carotene, Vitamin C, and Vitamin E, pharmaceutically acceptable salts of Vitamin A, carotene, Vitamin C, and Vitamin E, and the like, and mixtures thereof.

According to another preferred embodiment of the present invention the composition is provided for intravenous, intramuscular, spinal, epidural, transdermal, intranasal, mucosal, parenteral, oral, enteral or rectal administration.

Depending on the route of administration the pharmaceutical composition according to the present invention may be formulated, for instance, as tablets, capsules, liquids, infusion and suppositories (see e.g. "Pharmaceutical Formulation Development of Compounds" by Sven Frokjaer (1999), CRC; "Handbook of Pharmaceutical Manufacturing Formulations" by Sarfaraz K. Niazi (2004), CRC).

The peptides are preferably comprised in the composition in an amount between 0.1 µg/g to 100 mg/g, preferably 1 µg/g to 80 mg/g. In any way, the effective dosages for prevention or treatment of human patients can be optimised for given patients or patient collectives according to the routine methods available for the present field.

Another aspect of the present invention relates to the use of at least one peptide with neurotrophic and/or neurogenic activity as defined above which may be part of a molecule consisting of a maximum of 50, preferably a maximum of 40, more preferred a maximum of 30, even more preferred a maximum of 20, amino acids, and/or at least one peptide having an amino acid sequence selected from the group consisting of G-D-G-G-L-F-E-K (SEQ ID No. 5), G-L-F-E-K—K-L-W (SEQ ID No. 6), V-G-D-G (SEQ ID No. 7), G-D-G-G (SEQ ID No. 8), D-G-G-L (SEQ ID No. 9) and G-G-L-F (SEQ ID No. 10) for the manufacture of a medicament for the treatment and/or prevention of a neurodegenerative disease.

According to the present invention all peptides disclosed herein and exhibiting neurotrophic and/or neurogenic activity may be used for manufacturing a medicament for the treatment and/or prevention of neurodegenerative diseases.

According to a preferred embodiment of the present invention the peptide is a peptide according to the present invention as defined above.

The neurodegenerative disease is preferably selected from the group consisting of Alexander disease, Alper's disease, Alzheimer disease, Amyotrophic lateral sclerosis, Ataxia telangiectasia, Canavan disease, Cockayne syndrome, Corticobasal degeneration, Creutzfeldt-Jakob disease, epilepsy, Huntington disease, Kennedy's disease, Krabbe disease, Lewy body dementia, Machado-Joseph disease (Spinocerebellar ataxia type 3), Multiple sclerosis, Multiple System Atrophy, Parkinson disease, Pelizaeus-Merzbacher Disease, Pick's disease, Primary lateral sclerosis, Refsum's disease, Sandhoff disease, Schilder's disease, Spinocerebellar ataxia, Steele-Richardson-Olszewski disease, stroke, depression and Tabes dorsalis.

Next to these preferred neurodegenerative diseases the peptide according to the present invention may also be used to treat other cerebral disorders.

In one embodiment of the invention a peptide or protein comprising or consisting of a peptide of the present invention can be employed as a drug stimulating cerebral reparative process and used for the treatment and prevention of trauma-associated cerebral lesions, including the treatment of cerebral lesions after a fracture of the cranial vault, skull base, multiple bone fractures, the treatment for the cerebral lesions in cases of intracranial trauma (e.g. posttraumatic cerebral concussion, cerebral wounds and contusion, subarachnoid, subdural and extradural haemorrhage), the treatment and prevention of traumatic shock, the treatment of the cerebral lesions associated with the impact of radiation, lowered temperature, heat and light, air pressure, electric and ultrahigh frequency current, the treatment and prevention of delayed-onset effects of skull fractures, the treatment and prevention of delayed-onset effects of intral cranial trauma, the treatment and prevention of delayed-onset cerebral lesions induced by radiation, complications after surgical and other medical interventions.

In another embodiment of the present invention the peptides according to the present invention may be used as a drug suppressing toxic effects of the neurotrophic agents, stimulating cerebral repair processes and revealing cerebroprotective activity for the treatment and prevention of cerebral lesions after poisoning including the treatment of cerebral lesions after poisoning with therapeutic agents, medicinal and biological compounds, the treatment of the cerebral impairment with agents of non-medical origin, the treatment and prevention of delayed-onset cerebral lesions induced by poisoning with drugs and nonmedical substances.

In another embodiment of the present invention the peptides according to the present invention may be used as drug with nootropic activity and stimulating cerebral repair processes for the treatment and prevention of mental deficiencies.

In another embodiment of the present invention the peptides according to the present invention may be used for stimulating cerebral repair processes and motional activity for the treatment and prevention of paralytic disorders including the treatment and prevention of hemiplegia, the treatment and prevention of infantile cerebral paralysis, the treatment and prevention of other paralytic syndromes (quadriplegia, paraplegia, diplegia of upper extremities, monoplegia of lower extremities).

In another embodiment of the present invention the peptides according to the present invention may be used as drug stimulating cerebral repair processes with cerebroprotective activity for the treatment and prevention of cerebral impairments in case of chromosome anomalies including Down's syndrome.

In another embodiment of the present invention the peptides according to the present invention may be used as drug stimulating cerebral repair processes with cerebroprotective activity for the treatment and prevention of cerebral impairments in case of inflammatory cerebral disorders including the treatment and prevention of cerebral impairments in case of bacterial meningitis including *cryptococcus* meningitis in AIDS patients, the treatment and prevention of cerebral impairments in case of nonbacterial meningitis, the treatment and prevention of cerebral impairments in case of meningitis of unclear origin, the treatment and prevention of cerebral impairments in case of encephalitis, myelitis and encephalomyelitis, including cerebral toxoplasmosis in AIDS patients, for the treatment and prevention of cerebral impairments in case of intracranial abscesses, for the treatment and prevention of cerebral impairments in case of phlebitis and thrombophlebitis of intracranial venous sinus, for the treatment and prevention of sequalae after intracranial abscesses or purulent infection.

In another embodiment of the present invention the peptides according to the present invention may be used as drug stimulating cerebral repair processes with cerebroprotective and nootropic activity for the treatment and prevention of cerebral impairments in case of cerebral-vascular disorders including the treatment and prevention of cerebral impairments in case of subarachnoid haemorrhage, treatment and prevention of cerebral impairments in case of cerebral haemorrhage, the treatment and prevention of cerebral impairments in case of occlusion and Stenosis of precerebral arteries, the treatment and prevention of cerebral impairments in case of occlusion of cerebral arteries, the treatment and prevention of cerebral impairments in case of transitory cerebral ischemia, the treatment and prevention of cerebral impairments in case of other cerebral-vascular disorders (acute cerebral-vascular disorders, cerebral atherosclerosis and other generalised cerebral-vascular disorders, hypertension encephalopathy, cerebral aneurysm, cerebral arteritis and non-purulent thrombosis of intracranial venous sinus).

In another embodiment of the present invention the peptides according to the present invention may be used as drug stimulating cerebral repair processes, having cerebroprotective and nootropic activity for the treatment and prevention of alcoholic psychosis including the treatment and prevention of delirium tremens at abstinence syndrome, the treatment and prevention of alcoholic amnestic syndrome and other alcoholic dementia disorders, the treatment and prevention of pathologic alcoholic intoxication, the treatment and prevention of alcoholic paranoia and alcoholic psychosis of paranoid type.

In another embodiment of the present invention the peptides according to the present invention may be used as drug stimulating cerebral repair processes, having cerebroprotective and nootropic activity for the treatment and prevention of cerebral impairment in case of alcoholism.

In another embodiment of the present invention the peptides according to the present invention may be used as a drug suppressing toxic effects of neurotropic agents and having cerebro-protective and nootropic activity for the treatment and prevention of drug-induced psychosis including the treatment and prevention of the drug abstinence syndrome, the treatment and prevention of drug-induced paranoid and/or hallucinatory disorders, the treatment and prevention of pathologic intoxication with medical agents, the treatment and prevention of other drug-induced psychic disorders (delirium, dementia, amnestic syndrome and organic affective syndrome).

In another embodiment of the present invention the peptides according to the present invention may be used as a drug suppressing toxic effects of neurotropic agents and having cerebro-protective activity for the treatment and prevention of drug addiction including the treatment and prevention of addiction to opioid agents, the treatment and prevention of addiction to barbiturate, sedative agents and tranquillisers, the treatment and prevention of cocaine addiction, the treatment and prevention of addiction to *cannabis* and derivatives thereof, the treatment and prevention of addiction to amphetamine and psychostimulating agents, the treatment and prevention of addiction to hallucinogenic agents, treatment and prevention of cerebral impairments caused by drug abuse without drug addiction (abuse of alcohol, tobacco, *cannabis*, hallucinogens, opioids, cocaine, psychostimulating agents, antidepressants).

In another embodiment of the present invention the peptides according to the present invention may be used as an agent for treatment and prevention of psychogenic symptoms and syndromes including the treatment and prevention of psychogenic physiologic impairments, the treatment and prevention of other psychogenic symptoms and syndromes (stammering and impediments, psychogenic anorexia tics, repeated stereotype movements, inorganic sleep disorders, psychogenic diet disorders, enuresis, psychalgia), the treatment and prevention of acute stress response, the treatment and prevention of reactions induced by psychological directions.

In another embodiment of the present invention the peptides according to the present invention may be used as an agent for treatment and prevention of inorganic psychoses including the treatment and prevention of Schizophrenie disorders, the treatment and prevention of affective psychoses, the treatment and prevention of paranoid conditions, the treatment and prevention of other inorganic psychoses (psychoses of depressive and agitate types, reactive confusion, acute paranoid reactions, psychogenic paranoid psychoses) and non-differentiated psychoses including psychoses induced with cerebral impairments in AIDS patients, the treatment and prevention of infantile psychoses including infantile autism and disintegrative psychoses.

In another embodiment of the present invention the peptides according to the present invention may be used as a drug stimulating cerebral repair processes and having cerebroprotective and nootropic activity for the treatment and prevention of cerebral impairments in case of other cerebral disorders including the treatment and prevention of cerebral impairments in case of cerebral cysts, the treatment and prevention of hypoxic cerebral damage, the treatment and prevention of cerebral impairments in case of intracranial hypertension, the treatment and prevention of cerebral impairments in case of encephalopathy.

In another embodiment of the present invention the peptides according to the present invention may be used as drug stimulating cerebral repair processes and motional activity, having cerebroprotective and nootropic effects for treatment and prevention of symptoms and syndromes in case of various cerebral disorders including the treatment and prevention of cognitive disorders, memory and artention, impairments (for instance, in case of amnestic diseases, mental deficiency, inorganic psychoses, etc.), the treatment and prevention of aphasia and apraxia (for instance, in case of amnestic diseases, inorganic psychoses, cerebral impairments due to chromosome anomalies, etc.), the treatment and prevention of emotional disorders (for instance, in case of inorganic psychoses, demyelinising cerebral disorders, etc.), the treatment and prevention of psychopathologic syndrome (for instance, in case of transitional organic psychotic conditions, drug-induced psychoses, drug addiction, etc.), the treatment and prevention of asthenic-depressive syndrome (for instance, in case of inorganic psychoses, cerebral impairments due to chromosome anomalies, etc.), the treatment and prevention of delirium syndrome (for instance, in case of drug-induced psychoses and drug addiction, inorganic psychoses, etc.), the treatment and prevention of sleep disorders (for instance, in case of cerebral tumours, transitional organic psychotic conditions, etc.), for treatment and prevention of cerebral-focal syndrome (focal pathologic symptoms) (for instance, in case of cerebral impairments caused by complications of surgical or other medical intervention, demyelinising cerebral disorders, etc.), the treatment and prevention of syndrome of motor disorders (for instance, in case of cerebral tumours, cerebral impairments caused by poisoning, etc.), the treatment and prevention of peripheral neuropathy, preferably diabetic neuropathy.

According to a preferred embodiment of the present invention the medicament further comprises a pharmaceutical acceptable excipient and/or carrier as defined above.

According to another preferred embodiment of the present invention the composition further comprises at least one additional pharmaceutically active component.

The medicament is preferably provided for intravenous, intramuscular, spinal, epidural, transdermal, subcutaneous, intranasal, mucosal, parenteral, oral, enteral or rectal administration.

According to a preferred embodiment of the present invention the medicament comprises the peptide in an amount between 0.1 µg/g to 100 mg/g, preferably 1 µg/g to 80 mg/g.

It is in particular preferred to use as peptide in a medicament of the present invention a peptide having the amino acid sequence SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9 and/or SEQ ID No. 10.

Another aspect of the present invention relates to a method for preventing a break out of a neurodegenerative disease in an individual and for treating an individual suffering from a neurodegenerative disease comprising the administration of a pharmaceutical composition or of an effective amount of at least one peptide according to the present invention.

The term "effective amount" of a peptide as used herein will depend among other factors on the route of administration and physical condition of the individual to be exposed to said peptide. Methods for the determination of the effective amount are known to the skilled person.

The neurodegenerative disease is preferably selected from the group consisting of Alexander disease, Alper's disease, Alzheimer disease, Amyotrophic lateral sclerosis, Ataxia telangiectasia, Canavan disease, Cockayne syndrome, Corticobasal degeneration, Creutzfeldt-Jakob disease, epilepsy, Huntington disease, Kennedy's disease, Krabbe disease, Lewy body dementia, Machado-Joseph disease (Spinocerebellar ataxia type 3), Multiple sclerosis, Multiple System Atrophy, Parkinson disease, Pelizaeus-Merzbacher Disease, Pick's disease, Primary lateral sclerosis, Refsum's disease, Sandhoff disease, Schilder's disease, Spinocerebellar ataxia, Steele-Richardson-Olszewski disease, peripheral neuropathy, diabetic neuropathy, stroke, depression and Tabes dorsalis.

According to a preferred embodiment of the present invention the peptide is administered to said individual at a dose of 0.1 µg/kg to 20 mg/kg body weight, preferably 0.5 µg/kg to 10 mg/kg body weight.

Another aspect of the present invention relates to the use of at least one peptide with neurotrophic and/or neurogenic activity and/or at least one peptide having an amino acid sequence selected from the group consisting of G-D-G-G-L-F-E-K (SEQ ID No. 5), G-L-F-E-K—K-L-W (SEQ ID No. 6), V-G-D-G (SEQ ID No. 7), G-D-G-G (SEQ ID No. 8), D-G-G-L (SEQ ID No. 9) and G-G-L-F (SEQ ID No. 10) for the manufacture of a medicament for improving learning memory capacities in an individual.

Another aspect of the present invention relates to the use of a molecule consisting of a maximum of 50 amino acids with neurotrophic and/or neurogenic activity comprising at least one peptide according to the present invention or IPR-NEADGMPINV (SEQ ID No. 4) or a fragment thereof for the manufacture of a medicament for the treatment or enhancement of motor deficiencies in an individual.

BRIEF DESCRIPTION OF THE SEVERAL VIEWS OF THE DRAWING(S)

The present invention will be more fully understood and appreciated by reading the following Detailed Description in conjunction with the accompanying drawings, in which.

Figure 3A:
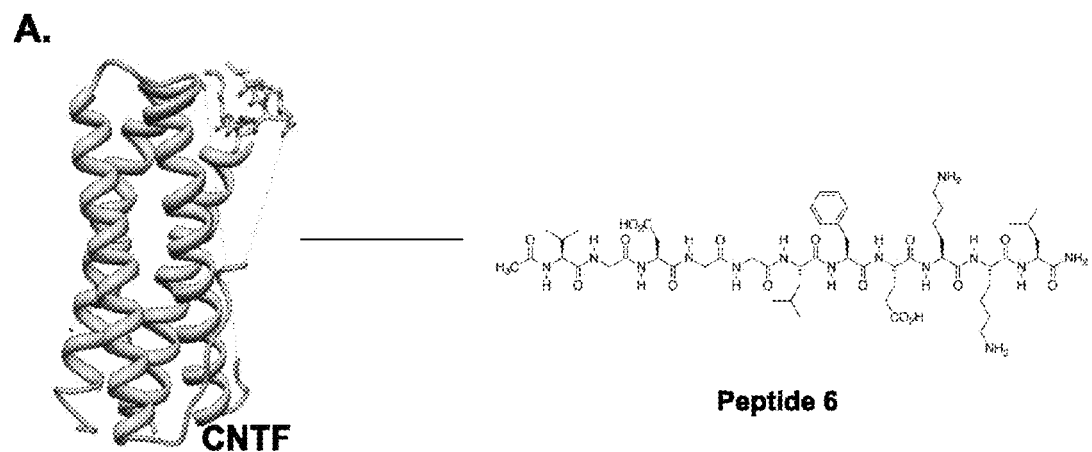
Figure 3B:
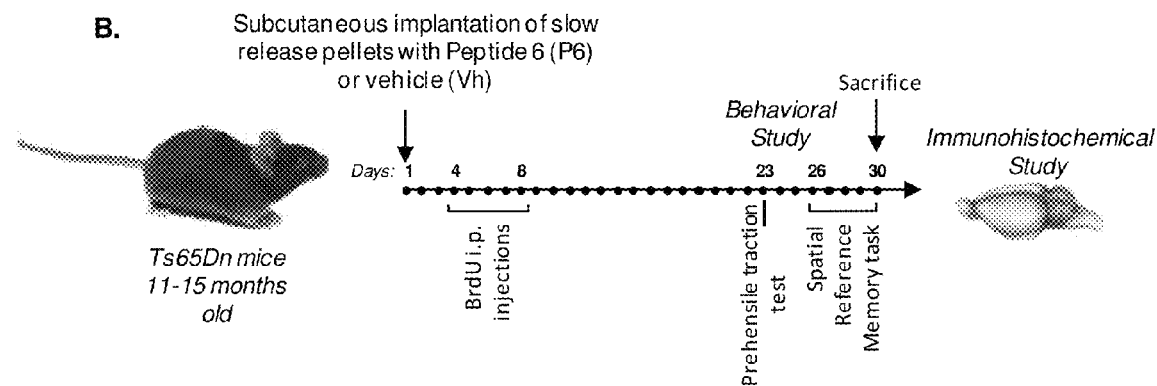
Figures 3C, 3D, 3E, 3F, 3G, 3H:
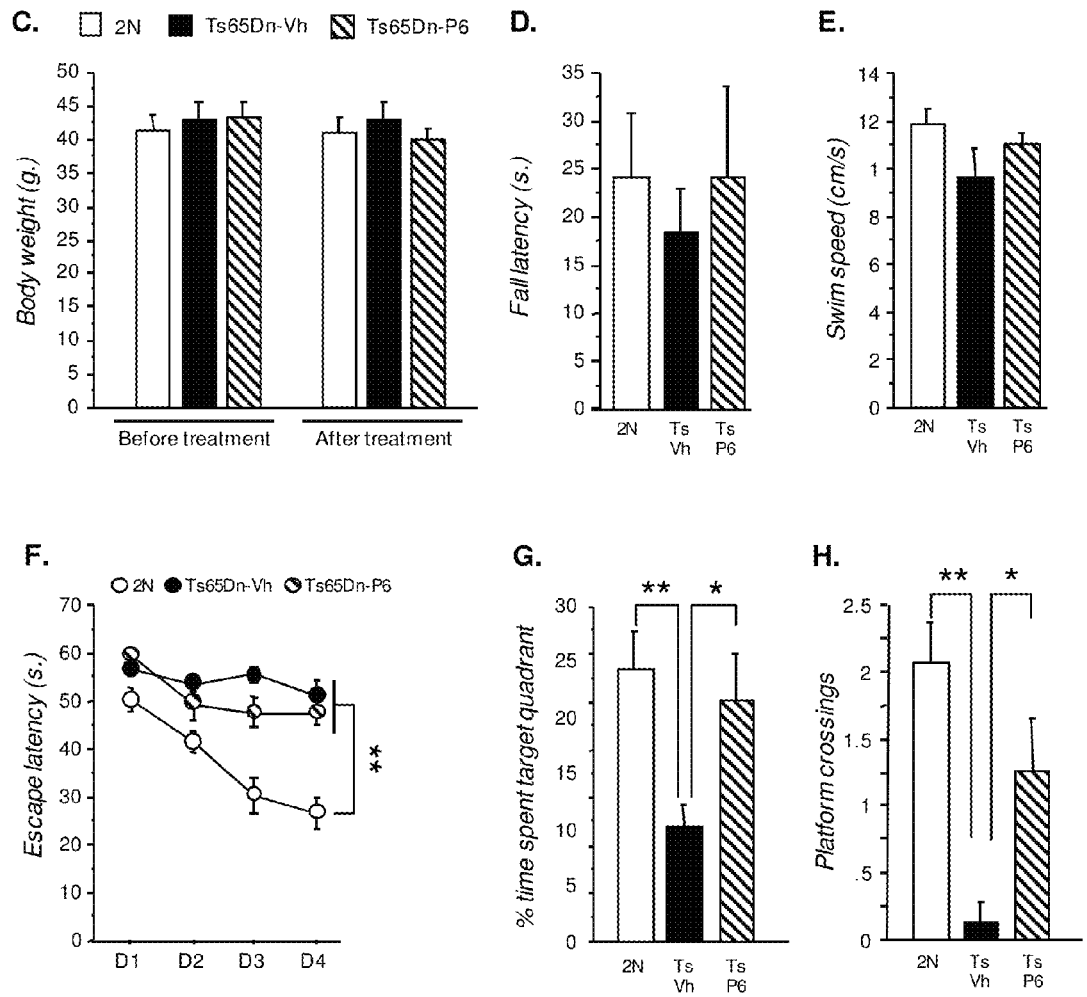

FIG. 3 is a series of graphs showing treatment with Peptide 6 did not induce adverse effects and alleviated cognitive impairment in Ts65Dn mice. FIG. 3(A) shows the position of Peptide 6 in ciliary neurotrophic factor (CNTF) and its structure via a Protein Database rendering of one 4-helix bundle of truncated CNTF (residues 2-287) generated from CNTF with only 1 protein chain is shown for clarity. Residues $^{149}$GGLFEKKL$^{156}$ (SEQ. ID. NO. 15) are shown as a tube model; the rest of the sequence is presented as a ribbon. The structure of Peptide 6 is also shown. FIG. 3 (B) shows the study design with BrdU. FIG. 3(C-E) shows that no significant changes of body weight, FIG. 3(C), no changes in the prehensile traction test (String test), FIG. 3(D), and no differences in swim speed in the spatial reference memory task, FIG. 3(E), were due to the treatment or the genotype. FIGS. 3(F-H) show that Ts65Dn mice were impaired compared with 2N mice during the spatial reference memory task training in the water maze, FIG. 3 (F). Treatment with Peptide 6 reduced this deficit because Ts65Dn mice significantly improved performance across days. During the probe trial of the spatial reference memory task, Ts65Dn mice were markedly impaired. Ts65Dn mice spent significantly less time in the target quadrant, FIG. 3(G), and crossed the platform location fewer times versus the 2N controls, FIG. 3(H). Treatment with Peptide 6 significantly restored performance of Ts65Dn mice to levels of the 2N controls, with *, p<0.050; , p<0.010; *, p<0.001.

Figure 4:
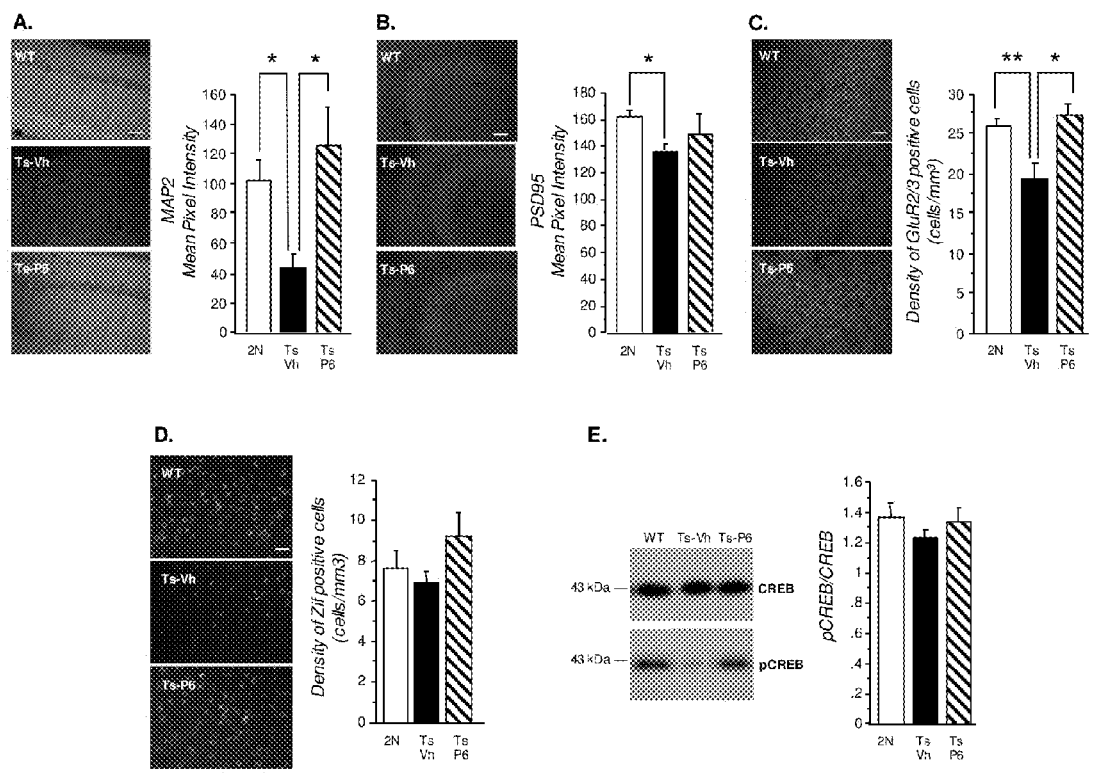

FIG. 4 is a series of graphs showing that treatment with Peptide 6 rescued neuronal plasticity in Ts65Dn mice. FIG. 4(A) shows treatment with Peptide 6 prevented the loss of dendritogenesis in the hippocampus of Ts65Dn mice. Left panel: photomicrographs illustrating effect of Peptide 6 on microtubule-associated protein 2(MAP2) density in CA1 of the hippocampus. Right panel: Ts65Dn mice displayed a significant reduction of MAP2 density in the hippocampus; treatment with Peptide 6 increased MAP2 density to control levels. *, p<0.050. FIGS. 4(B, C) show treatment with Peptide 6 rescued postsynaptic and AMPA receptor deregulation in the hippocampus of Ts65Dn mice. FIG. 4(B) Left panel: Photomicrographs illustrating effect of Peptide 6 on postsynaptic density protein 95 (PSD95) density in the CA3 of the hippocampus. FIG. 4(B) Right panel: Ts65Dn mice had a significant reduction of PSD95 proteins in the hippocampus that was increased by treatment with Peptide 6. FIG. 4(C) Left panel: Photomicrographs illustrating effect of Peptide 6 on glutamate receptors 2/3 (GluR2/3) density in the CA3 of the hippocampus. FIG. 4(C) Right panel: Density of GluR2/3 was dramatically decreased in the hippocampus of Ts65Dn mice, but treatment with Peptide 6 rescued this impairment. FIG. 4(D, E) Treatment with Peptide 6 increased activation of immediate early genes in Ts65Dn mice. FIG. 4(D) Left panel: Photomicrographs illustrating effect of Peptide 6 on density of Zif-positive cells in the CA1 region of the hippocampus. FIG. 4(D) Right panel: In the CA1 of the hippocampus, treatment with Peptide 6 tended to increase the number of Zif-positive cells in Tg65Dn mice. FIG. 4(E) Left panel: Representative Western blots from 1 animal from each group; blots developed with pCREB and CREB antibodies showed the level of CREB activity in Ts65Dn mice. FIG. 4(E) Right panel: Treatment with Peptide 6 tended to rescue activation of CREB in the hippocampus of Ts65Dn mice. WT, wild type; Ts-Vh, vehicletreated Ts65Dn mice; TsP6, Peptide 6—treated Ts65Dn mice. Scale bars=FIGS. 4(A-D) 20 µm.

Figure 5:
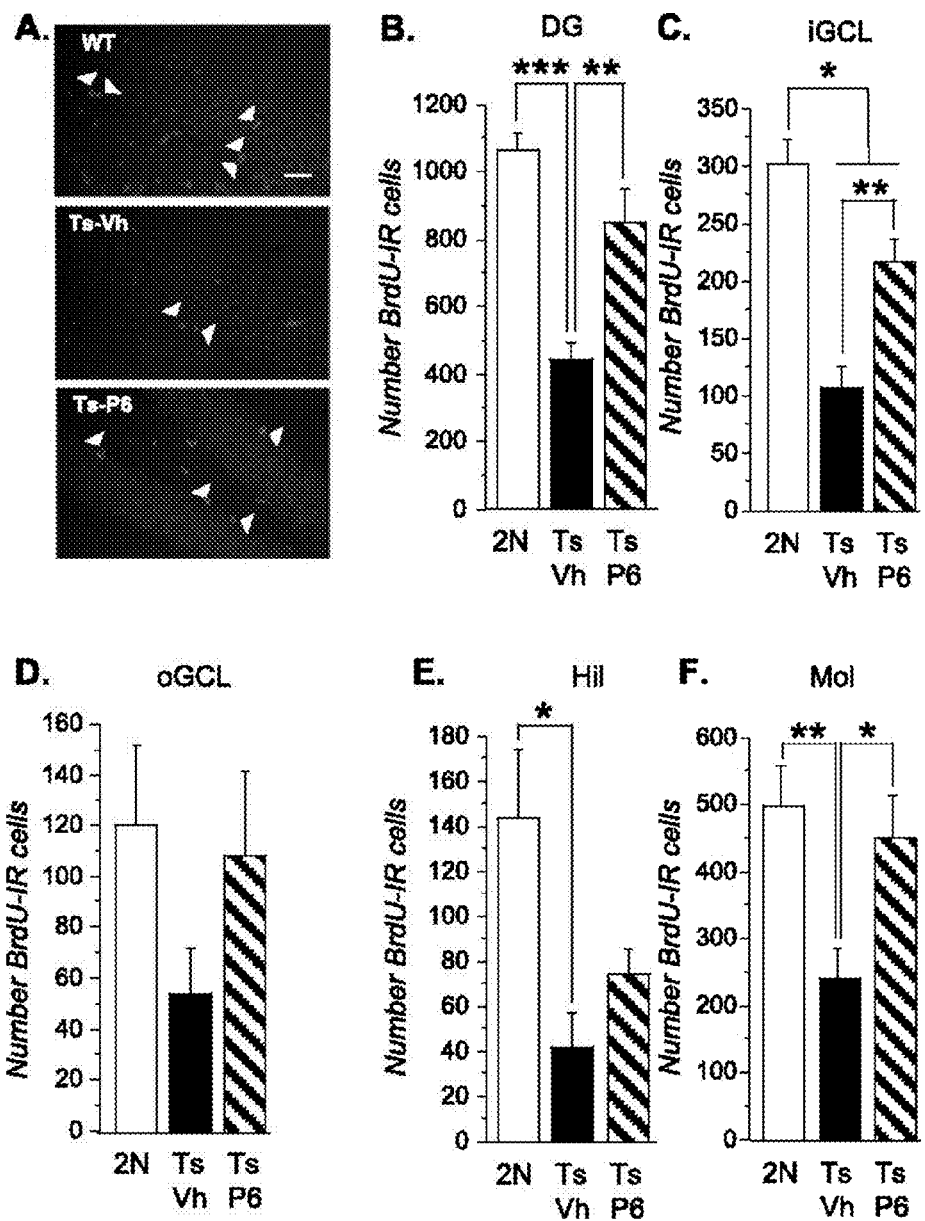

FIG. 5 is a series of graphs showing that treatment with Peptide 6 increased proliferation of neuronal progenitor cells in Ts65Dn mice. FIG. 5 (A) are photomicrographs illustrating effect of Peptide 6 on neural cell proliferation (BrdU-positive cells; white arrowheads) in the dentate gyrus (DG) with scale bar=20 µm. FIG. 5(B) is a chart showing neurogenesis in the DG was markedly impaired in Ts65Dn mice, but treatment with Peptide 6 restored the number of BrdU-immunoreactive cells to 2N control level. FIGS. 5(C-F) show the pool of newborn cells was significantly reduced in the inner granular cell layer (iGCL) (C), the hilus (E), and the molecular cell layer (F) of the DG in Ts65Dn mice. In the outer granular cell layer, oGCL, FIG. 5(D), there was a decrease of the number of BrdU-immunopositive cells in Ts65Dn mice versus 2N controls, but this effect did not reach significance. *, p<0.050; , p<0.010; *, p<0.001. BrdU, bromodeoxyuridine.

FIG. 6(a) shows the experimental design of Example 3; (b) and (c) show the proliferation of progenitors in four sub-regions of the hippocampus (for anatomical definitions, see "Materials and Methods" section): iGCL (inner granule cell layer, which included the subgranular zone [SGZ]), oGCL (outer granule cell layer), Mol (molecular layer) and Hil (hilus), revealed that compared to control group, CNTF 6c increased the number of BrdU-IR cells in the iGCL by 45% ($p<0.001$, Student's t-test), whereas no significant differences were observed in either oGCL, Mol or Hil.

Figure 7:
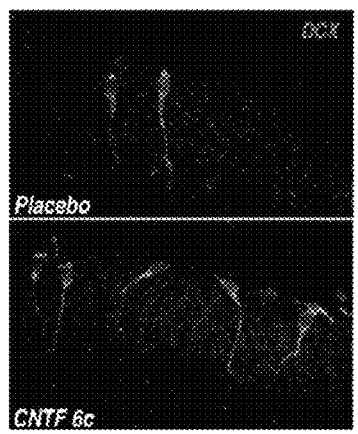
Figure 7:
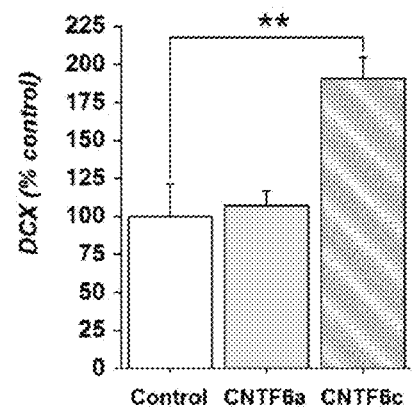
Figure 7:
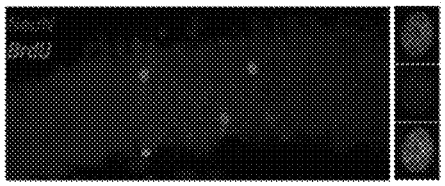
Figure 7:
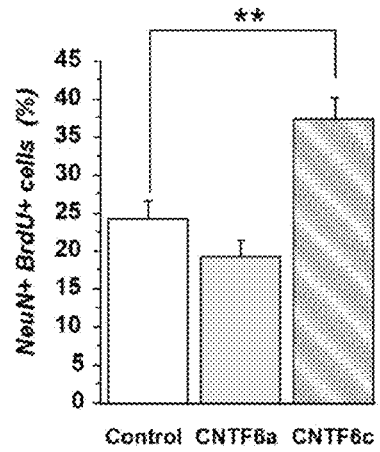

FIG. 7 shows the proliferation of immature neurons in the dentate gyrus (a) and the neuronal differentiation of progenitor cells in the dentate gyrus (b).

Figure 8:
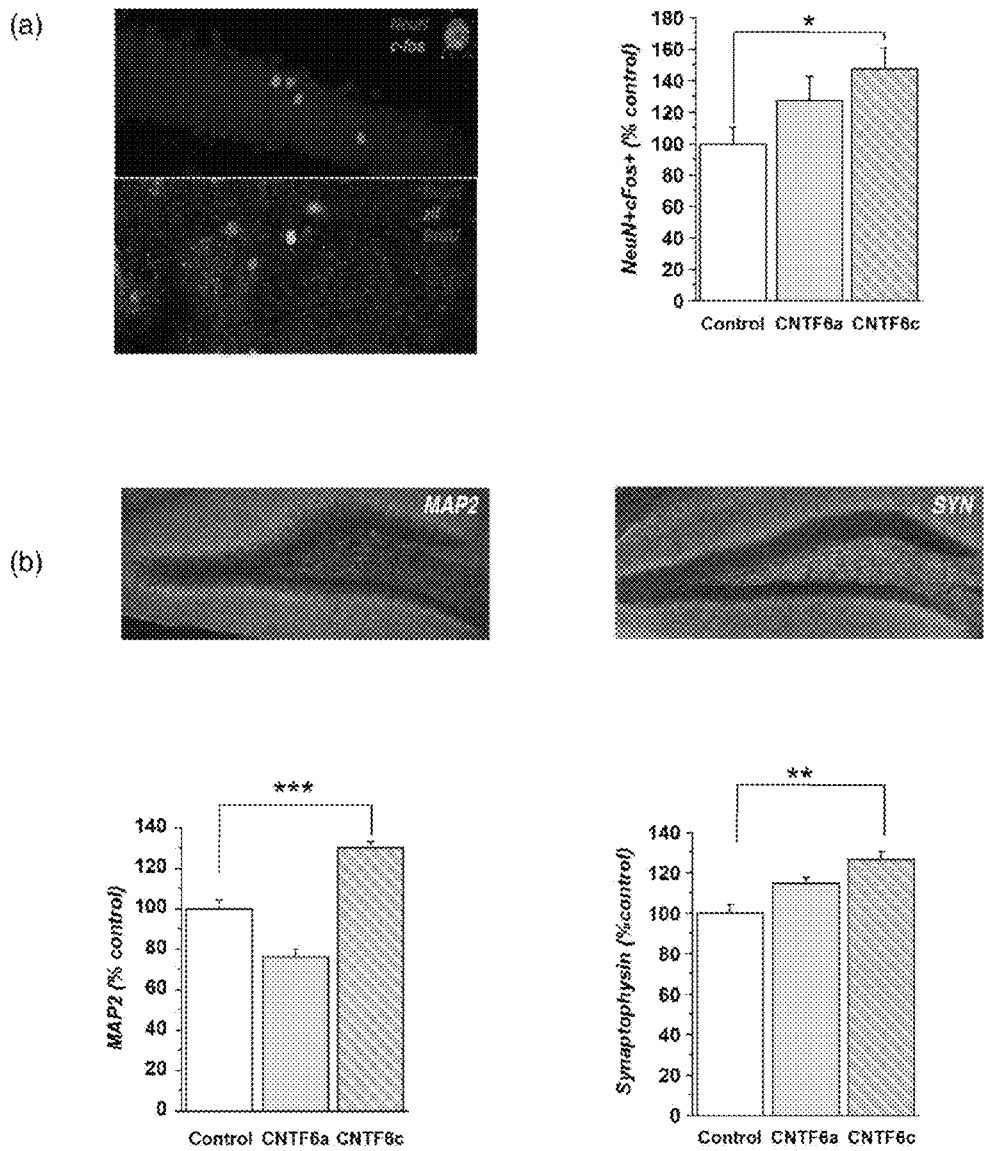

FIG. 8 shows the induction of immediate-early gene expression in resident neurons (a) and neurotrophy and neuroprotection in the dentate gyrus (b).

Figure 9:
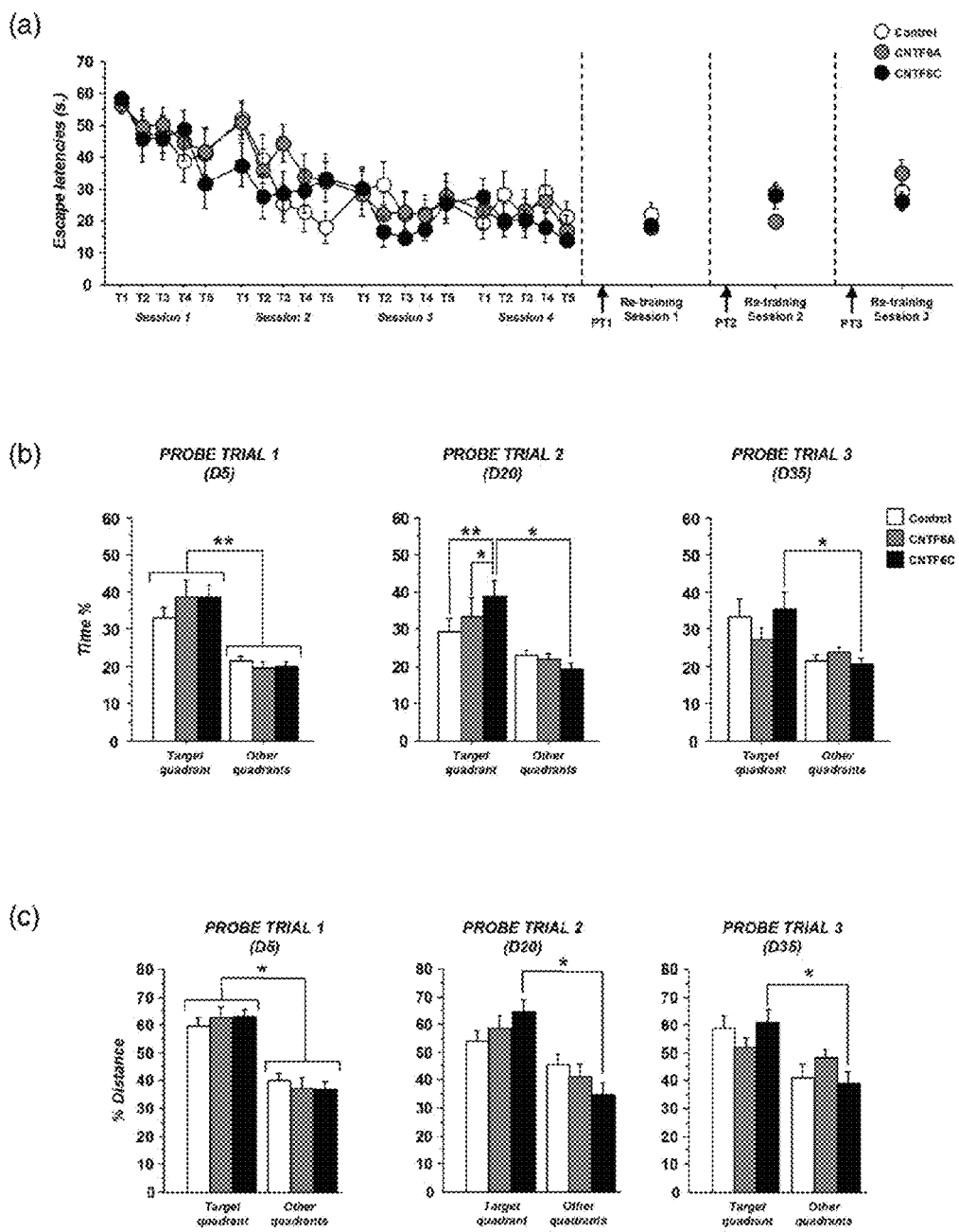

FIG. 9 shows the enhancement of memory by the administration of CNTF 6a and 6c.

Figure 10:
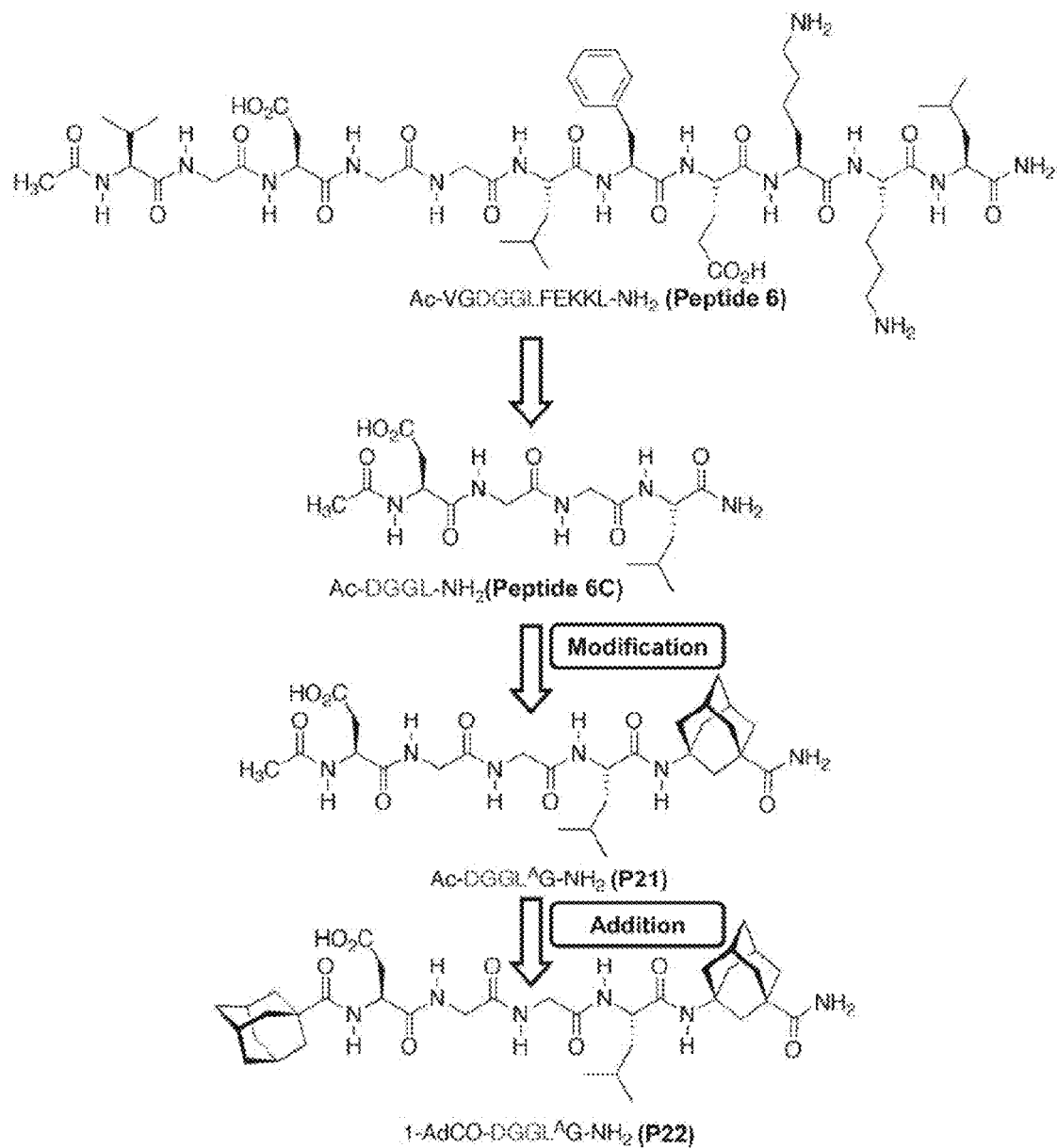

FIG. 10 shows the design and structures of neurogenic peptidergic compounds incorporating adamantane building blocks. From the neurogenic undecamer Ac-VGDG-GLFEKKL-NH$_2$ (SEQ ID NO:1) (Peptide 6) a truncated, still neurogenic tetramer Ac-DGGL-NH$_2$ (SEQ ID NO:9) (Peptide 6c) was designed. Addition of an unnatural amino acid based upon adamantane to the C-terminus of this subsequence via SPPS methods produced Ac-DGGL$^A$G-NH$_2$ (P21) (SEQ ID NO:12); capping of the N-terminus of P21 with adamantane-1-carboxylic acid yielded 1-AdCO-DG-GL$^A$G-NH$_2$ (P22) (SEQ ID NO:13)

Figure 11:
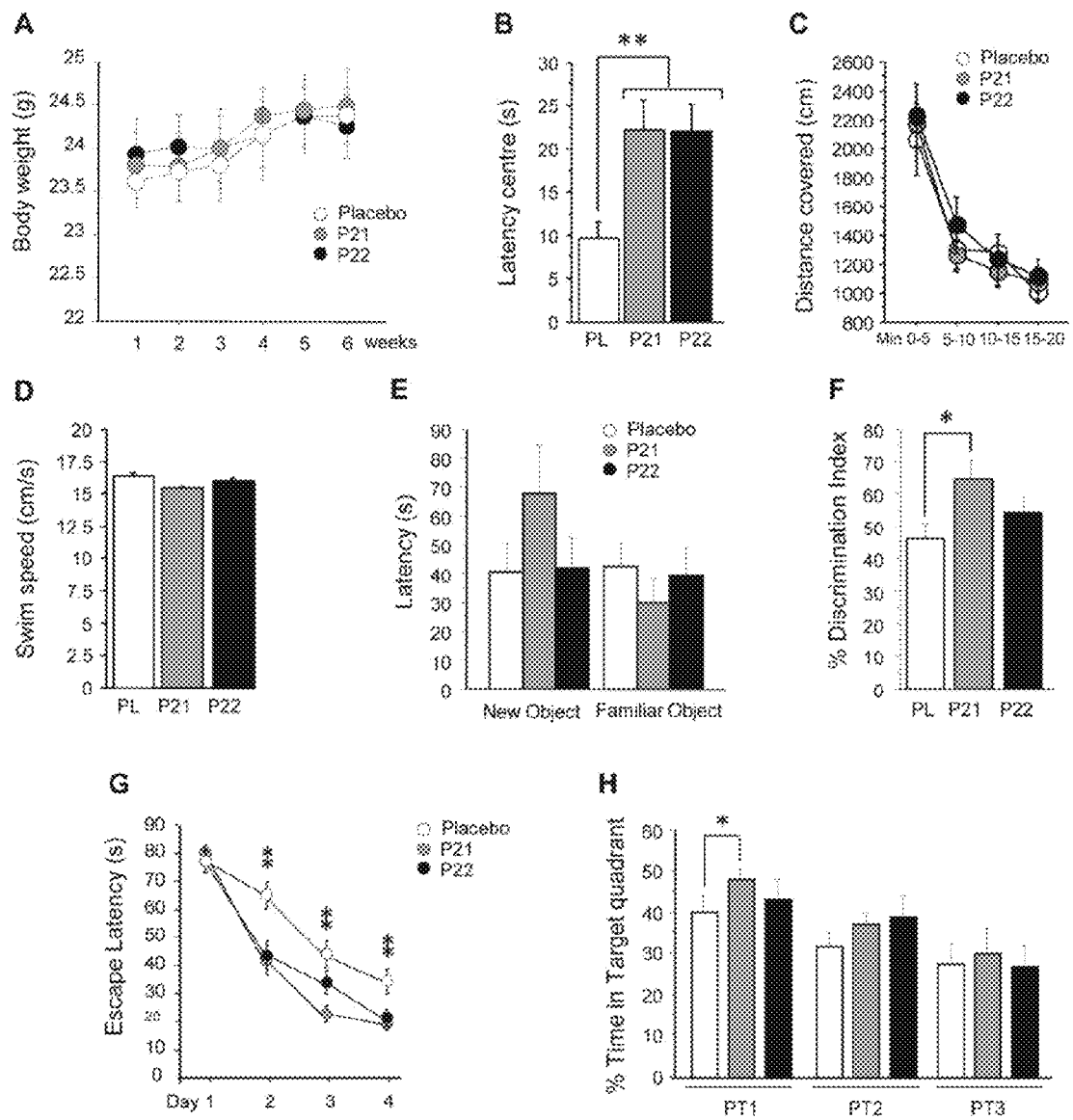
Figure 12:
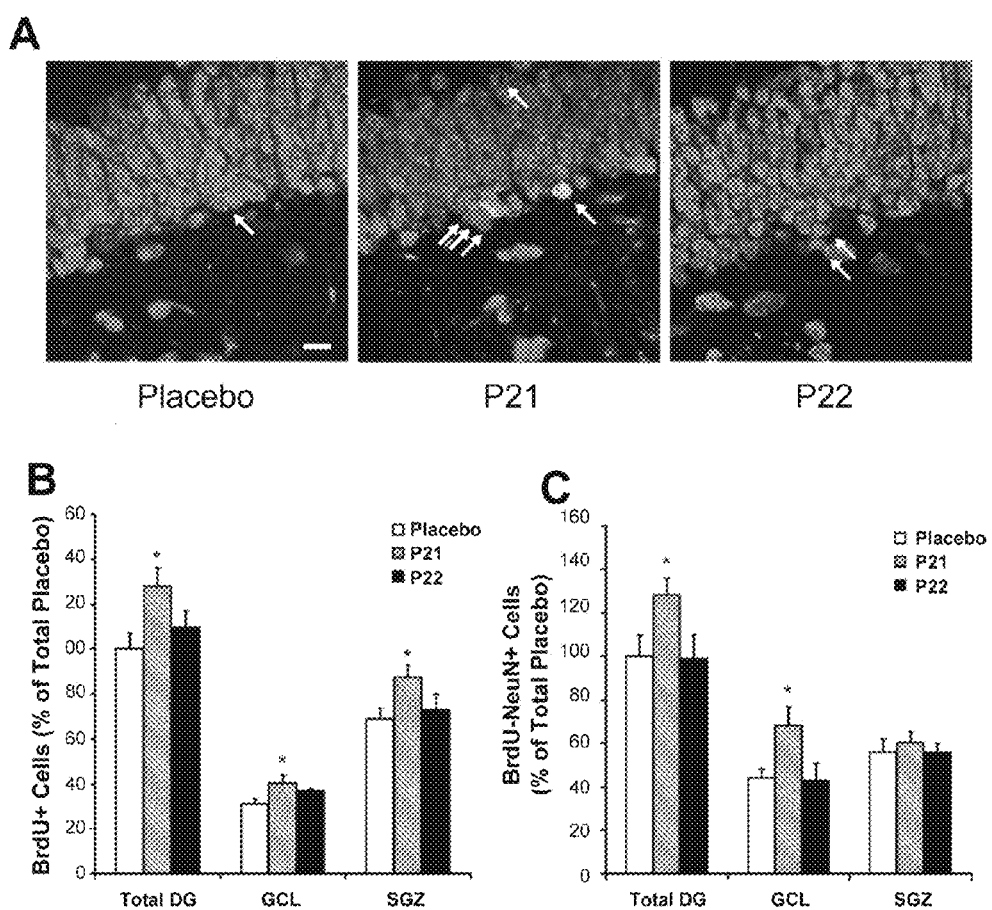
Figure 13:
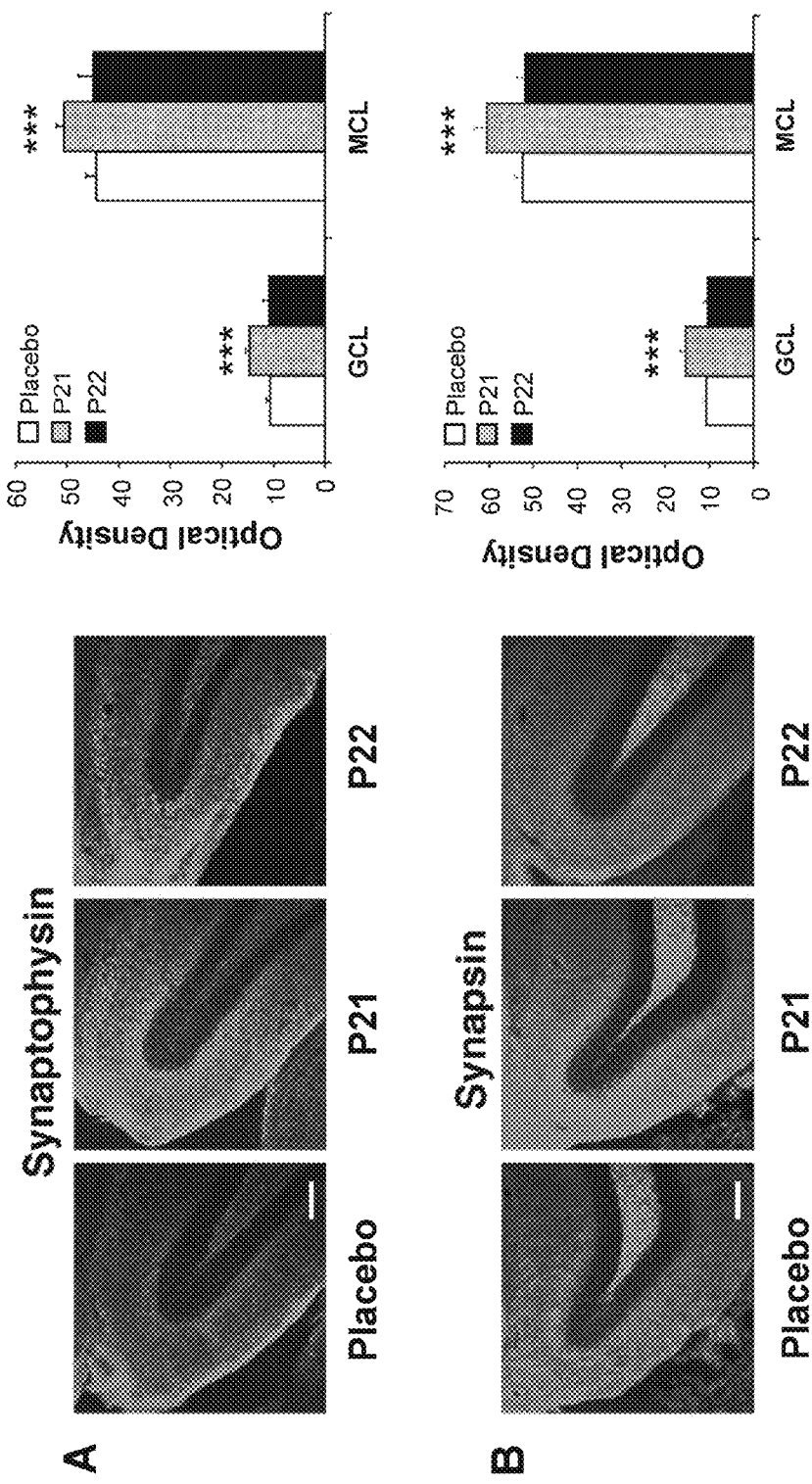

FIG. 11 shows that peptides incorporating $^A$Gly improve cognition. P21 and P22 did not induce any effect on body weight (A), exploratory activity (C) or swim speed (D) but reduced anxiety level of mice (B). (E-F) P21 significantly improved the ability to discriminate a new object versus a familiar object. *$p<0.05$; Student's t-test. (G) P21 and P22 increased performance in the learning of spatial memory task in water maze. **$p<0.001$; two-way ANOVA with post hoc Fisher LSD test. (H) P21 improved performance in the first probe trial, but treatment with P21 showed no effect 15 days (PT2) or 30 days (PT3) after the end of the treatment. *$p<0.05$; Student's t-test FIG. 12 shows that compound P21 promotes neurogenesis in the DG. (A) Representative picture of double labeled BrdU (red) and NeuN (green) positive cells. Scale bar represents 20 μm. (B) Numbers of BrdU positive cells were significantly increased in P21 treated animals in the total DG, GCL and in the SGZ (C) P21 treatment significantly increased the number of BrdU/NeuN positive cells in the GCL and in the total DG. *$p<0.05$, two-way ANOVA and post hoc Fisher LSD test FIG. 13 shows that compound P21 promotes synaptic plasticity in the DG. P21 significantly promoted expression of synaptophysin (A) and synapsin I (B) in the GCL and the MCL of the DG. ***$p<0.001$, two-way ANOVA and post hoc Fisher LSD test. Scale bars represent 100 μm.

Figure 14:
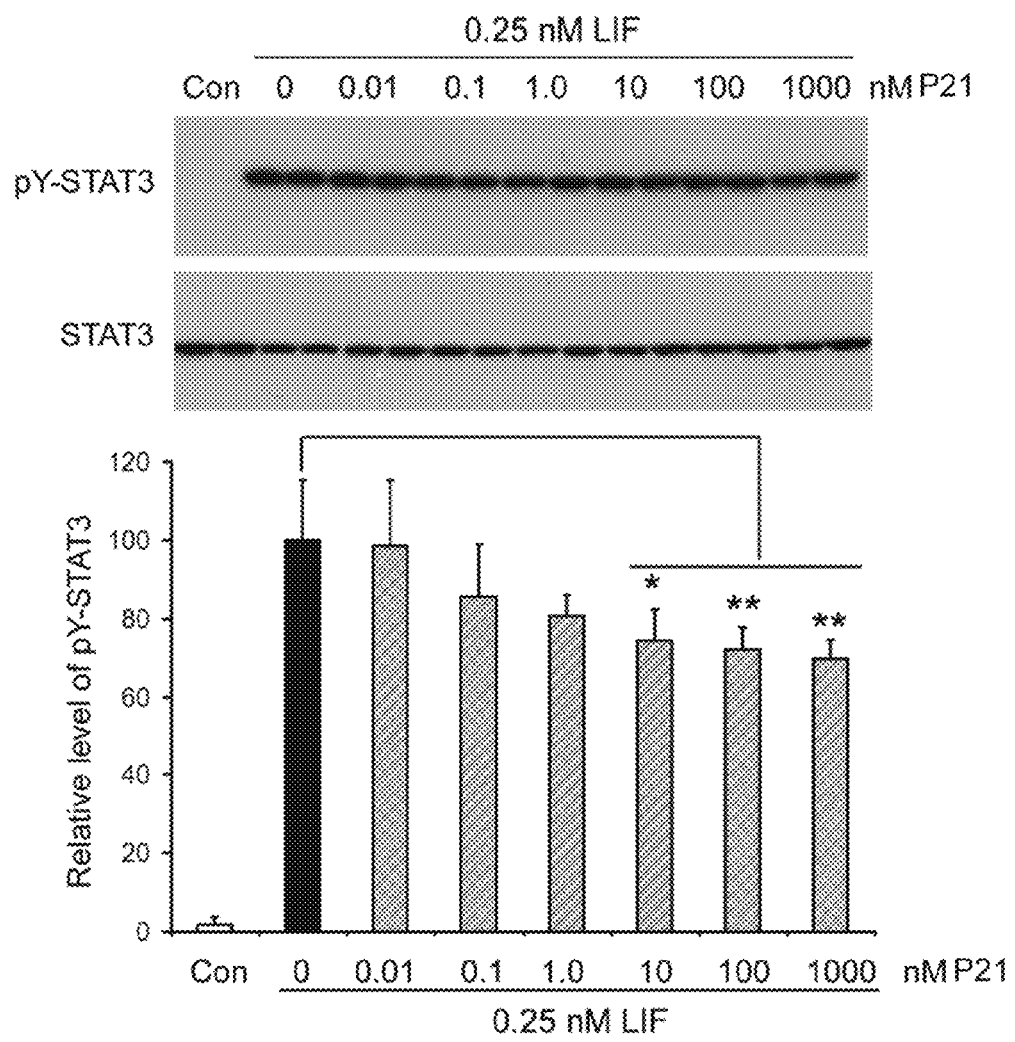

FIG. 14 shows the inhibition of LIF-induced STAT3 phosphorylation by P21 in a dose-dependent manner in HepG2 cells. HepG2 cells were treated with different concentrations of P21 together with 0.25 nM LIF for 15 min, and then the STAT3 phosphorylation at Tyr705 (pY-STAT3) was determined by Western blots. The pY-STAT3 value was normalized to total STAT3 expression. Data are presented as percentages of the value from cells treated with 0.25 nM LIF alone (100%). *$p<0.05$; **$p<0.01$.

DETAILED DESCRIPTION OF THE INVENTION

As described in co-pending application Ser. No. 13/044,323, hereby incorporated by reference, the ciliary neurotrophic factor (CNTF) peptide referred to as Peptide 6 and having the sequence VGDGGLFEKKL (SEQ ID No. 1), which comprises residues 145-155 of CNTF (or residues 146-156 if the starting amino terminal methionine is counted), was found to be neurogenic and neurotrophic, as well as blood-brain-barrier permeable with an in vitro plasma stability and a half-life of over six hours.

EXAMPLE 1

Figure 1:
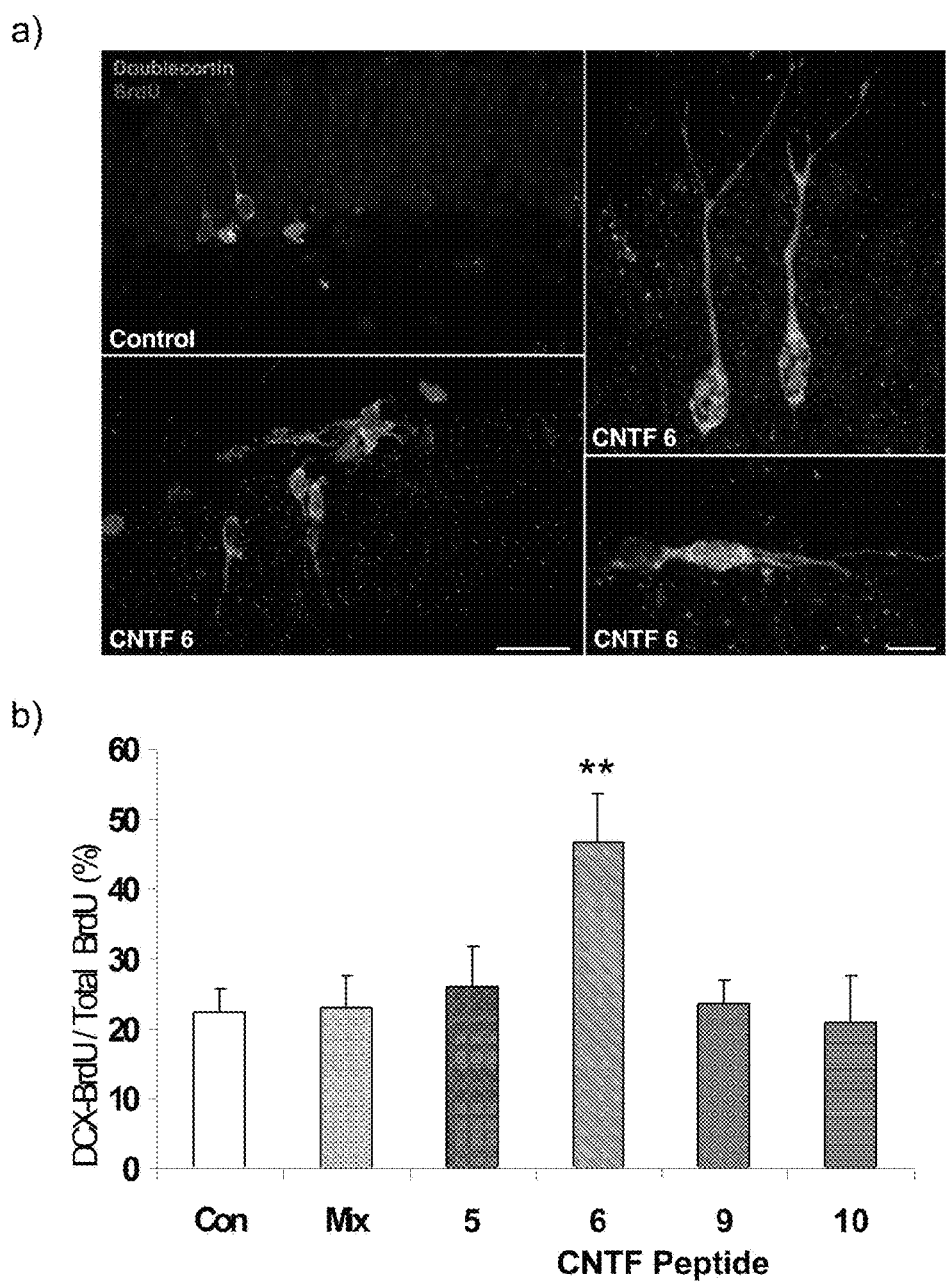
FIG. 1 shows the effect of Peptides 5, 9 and 10 on the expression of DCX in BrdU, bromodeoxyuridine, labeled progenitors in the dentate gyrus.
Figure 2:
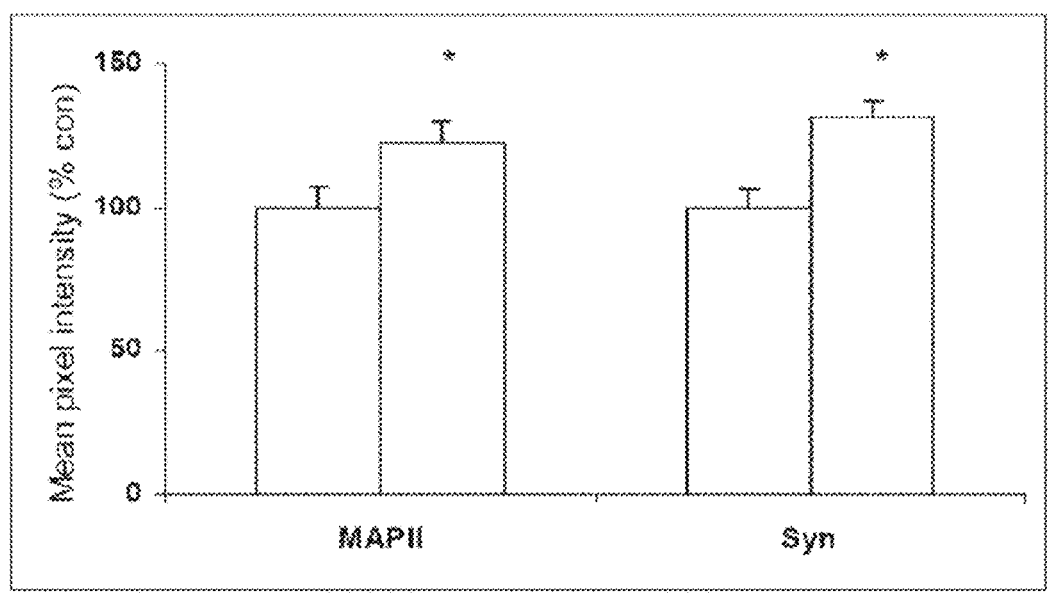
FIG. 2 shows the MAP2 and synaptophysin immunoreactivity in the dentate gyrus when Peptide 6 is administered.

Efficacy of the present invention in improving cognitive impairment has been established in animal models. More particularly, Peptide 6 induced a two fold increase in the differentiation of dentate gyrus progenitors into DCX (doublecortin) expressing cells in a 14 day treatment group of the mouse model C57/BL6. As seen in FIG. 1, Peptides 5, 9 and 10 did not have any effect on the expression of DCX in BrdU labeled progenitors in the dentate gyrus. As seen in FIG. 2, Peptide 6 also caused a statistically significant increase in MAP2 and synaptophysin immunoreactivity in the dentate gyrus of treated mice as measured by mean pixel intensity in the outlined area of interest.

Behavioral tests employing Morris Water maze task-based memory acquisition, retention and recall paradigms have also been carried out. Two groups of 18 mice each were treated with Peptide 6/Placebo containing implantable subcutaneous pellets with user specified timed release kinetics: 14 days for group 1 and 30 days for group 2. In particular, the 30 day group showed significant improvement in memory acquisition as evaluated by time spent in the target quadrant and distance covered in the target quadrant in the Morris Water Maze task.

All experiments involving mice were done on 8-10 month old female retired breeders of C57BL6 background. A total of 33 mice were divided into 10 groups of 3 animals each (except control group which had 6 mice). The groups are described in Table 1. Details of CNTF peptides are described in Table 2.

TABLE 1

| Group | Description | Concentration | # of mice |
|---|---|---|---|
| 1 | Control [normal saline] |  | 6 |
| 2 | Peptide mix | 0.5 nmal | 3 |
| 3 | Peptide 5-1 | 0.5 nmal | 3 |
| 4 | Peptide 5-2 | 5 nmal | 3 |
| 5 | Peptide 6-1 | 0.5 nmal | 3 |
| 6 | Peptide 6-2 | 5 nmal | 3 |
| 7 | Peptide 9-1 | 0.5 nmal | 3 |
| 8 | Peptide 9-2 | 5 nmal | 3 |
| 9 | Peptide 10-1 | 0.5 nmal | 3 |
| 10 | Peptide 10-2 | 5 nmal | 3 |

TABLE 2

| CNTF Peptide | Position in CNTF | MW | SEQ. ID No. |
|---|---|---|---|
| Peptide 5 | 133-145 | 1384 | 4 |
| Peptide 6 | 145-155 | 1203 | 1 |
| Peptide 9 | 91-102 | 1427 | 2 |
| Peptide 10 | Loop | 1192 | 11 (CHQGCGGLFEC) |

The animals were kept in groups of 3 per cage. The mice were given daily intraperitoneal injections of four CNTF peptides either separately or in a mixture for 2 weeks as described in Table 1. From day 2, BrdU (Bromodeoxyuridine;

150 mg/Kg) was added to the injections. The animals were sacrificed 24 hours after the last injection. Briefly, the animals were perfused transcardially with PBS and their brains taken out and dissected into halves. One hemisphere from each animal was frozen for biochemical analysis and the other was fixed in 4% paraformaldehyde for 48 hours followed by equilibration in 30% sucrose in PBS overnight. These were then processed for immuno-histochemistry.

Fixed tissues were cut into 40 pm sections on a freezing sliding microtome. One in 5 sections per brain was processed for BrdU staining and visualized by immunoflorecence. Cell counting was done on these sections to determine the number of BrdU labeled cells (representing newly born cells) in the dentate gyrus of the hippocampus. The area of counting was limited to the granule cell layer and the subgranular zone (a two-nucleus thick layer adjacent to the granule cell layer). For counting purposes, the dentate gyrus was divided into two areas, the outer granule cell layer (oGCL) consisting of out half of the granule cell layer, and the subventricular zone (SVZ) comprising of the inner half (towards the hilus) of the granule cell layer plus a two-nucleus thick layer adjacent to the outer border of the hilus. Cell counting was done on confocal images of the sections according to the optical dissector principle. Volumetric analysis was carried out with the help of Image Pro software.

EXAMPLE 2

Peptide 6 in Ts65Dn Mice

Peptide 6, which corresponds to amino acid residues 146 to 156 of human CNTF (FIG. 1A), was identified as an active region of this neurotrophic factor by epitope mapping of neutralizing antibodies to CNTF (40). The peptide was synthesized on a commercial basis by the Pan Biotechnology Facility of Stanford University (Palo Alto, Calif.).

Female Ts65Dn mice carrying a partial trisomy of chromosome 16 (18) were obtained from Jackson Laboratories (New Harbor, Me.) and maintained keeping the original genetic background by mating them with C57BL/6JEix C3SnHeSnj (B6EiC3) males. Mice were housed and bred in accordance with approved protocols from our Institutional Animal Care and Use Committee, according to the PHS Policy on Human Care and Use of Laboratory Animals (revised Mar. 15, 2010). This study was performed on heterozygous Ts65Dn female mice. When genotyped, each animal was checked for retinal degeneration. Mice carrying the gene for retinal degeneration were not used in the study. Control animals were nontrisomic (2N) littermate mice. Animals were group-housed (4 animals per cage) with a 12:12-hour light:dark cycle and with ad libitum access to food and water.

Female Ts65Dn mice 11- to 15-month-old (n=8) and 2N female littermates (n=8) received subcutaneous implants of extended release depot pellets containing Peptide 6 (Innovative Research of America, Sarasota, Fla.) for 30 days of continuous dosing (50 nmol per mouse per day). The dosage was chosen according to the titrations studied in previous work (40). For control groups, the pellets consisted of the carrier biopolymer only (Ts65Dn, n=7; 2N, n=7). For implantation, mice were anesthetized with 2.5% Avertin (0.38 ml for a 25-g animal; Sigma Aldrich). Under sterile conditions, pellets were subcutaneously implanted along the anterolateral aspect of the right shoulder with a precision trochar (Innovative Research of America). Animals were then transferred to the animal colony after recovery from anesthesia. There were no complications associated with the implantation and treatment. To investigate neural progenitor cell proliferation, bromodeoxyuridine (BrdU) was given as 2 daily intraperitoneal injections (75 mg/kg per dose) for 5 days starting on Day 4 of treatment with Peptide 6, as seen in FIG. 3B.

The physical state and condition of animals were carefully checked throughout the treatment by evaluating grooming, posture, physical state, and clasping reflex. Body weights were also recorded.

At the end of the treatment period, prehensile traction force was evaluated measuring fall latency of the mouse suspended with its forepaws from a string suspended 60 cm from a padded surface.

Before training, mice were handled gently for 2 to 3 min/d for 3 days to minimize nonspecific stress. Spatial reference memory testing was started on the last week of treatment (FIG. 3B). Spatial reference learning and memory were evaluated in the water maze using a procedure adapted from Morris et al. The test required that mice used a spatial navigational strategy based on a spatial representation of the environment to find a fixed submerged platform. The procedure was performed in a 110-cm-diameter circular tank. The pool was filled with water (21° C.±1° C.) made opaque by adding white nontoxic paint. Acquisition was started with the escape platform (10-cm-diameter submerged 1 cm below water surface) in the Northwest quadrant; each animal was given 60 seconds to find the platform. If the mouse did not find the platform in 60 seconds, it was gently guided to it. At the end of each trial, the mouse was left on the platform for 20 seconds, then dried and returned to its home cage until the next trial. Five such acquisition trials were given on each day for 4 consecutive days. A test for retention, or probe trial, was given 24 hours later. During the probe trial, the mouse was allowed to swim in the tank without the escape platform for 60 seconds.

The learning measures were the time and distance covered to reach the escape platform. Swim speed was also calculated. For the probe trial, the tank was divided into 4 imaginary quadrants and a small zone where the escape platform was located. The measures for retention were the percent of time spent in each quadrant and the number of crossings of the platform zone. Behavior in the water maze was monitored by a Samsung Digital Camera (SDC 4304, San Diego Instruments, San Diego, Calif.) mounted to the ceiling and tracked and timed by a SMART (Pan Lab/San Diego Instruments) version 2.0.14 software.

Within 90 minutes after completion of the behavioral task, animals were anesthetized with an overdose of sodium pentobarbital (125 mg/kg) and transcardially perfused with 0.1 mol/L phosphate-buffered saline (PBS). After perfusion, the brains were removed, and the hippocampus, a portion of the cortex, the cerebellum, and thalamic nuclei were dissected from the left hemisphere and immediately frozen in dry ice for biochemical analysis. The right hemisphere was fixed in 4% paraformaldehyde in 0.1 mol/L PBS for at least 24 hours at room temperature. Tissues were then postfixed in a 30% sucrose solution at 4° C. overnight. Forty-micrometer sagittal sections of the entire hippocampus were cut on a freezing microtome. The sections were stored in glycol antifreeze solution (ethylene glycol, glycerol, and 0.1 mol/L PBS in 3:3:4 ratio) at −20° C. until further processing.

For the immunohistochemical study, 4 animals per group were randomly selected and analyzed. Immunohistochemistry was performed on free-floating sections as described (42). Briefly, every 10th section was chosen for densitometry (~5-6 sections per animal), and every 5th brain section was chosen for quantification of newborn cells (10-11 sections per animal).

The following primary antibodies were used: SMI52 to the adult isoforms of microtubule-associated protein 2 (MAP2, MAP2a/b, 1:1000; Covance, Princeton, N.J.); anti-postsynaptic density protein 95 (PSD95; Cell Signaling Technology, Danvers, Mass.); anti-glutamate receptors 2/3 (GluR2/3; Abcam, Cambridge, Mass.), anti-Zif268 (1:500; Calbiochem, San Diego, Calif.), and anti-BrdU (1:400; Accurate, Westbury, N.Y.). The following secondary antibodies were used: Alexa 488—conjugated goat anti-mouse immunoglobulin G antibody (1:500; Molecular Probes, Carlsbad, Calif.) and Alexa 594—conjugated goat anti-rabbit immunoglobulin G antibody (1:500; Molecular Probes).

For MAP2 and PSD95 densitometry, the region of interest was outlined at a magnification of 20×; the entire area of the CA1, the CA3, and the dentate gyrus (DG) of the hippocampus and parietal association cortex was analyzed. Maximum projection images were then generated based on confocal z stacks, and the antibody staining was quantified by measuring mean pixel intensity with the software ImageProPlus 5.0 (Media Cybernetics, Silver Spring, Md.).

Zif268- and GluR2/3-positive cells were counted using Stereo Investigator software (Microbrightfield, Inc, Williston, Vt.). Areas of interest were traced at low magnification with a 10× objective, and counting frames were selected at random by the software. An optical fractionator method was used to estimate the number of positive cells at high magnification with a 40× objective. This technique involved counting neurons with an optical dissector, a 3-dimensional probe placed through a reference space (43). This method is independent of volume measurements and is therefore unaffected by tissue shrinkage. A total of 3 to 4 sections per region were analyzed, and the final cell counts were expressed as cells per cubic millimeter. Neurons were considered stained when their edges lay within the dissector area and they did not intersect forbidden area. The guard zone thickness was set as 2 μm.

Neural progenitor cell proliferation was assessed in the DG by counting the number of BrdU-immunoreactive (BrdUIR) cells in various layers of the DG. The granule cell layer (GCL) was subdivided into inner and outer halves. The inner GCL consisted of the subgranular zone, defined as a 2- to 3-nuclei-thick layer bordering the inner half of the GCL adjacent to the hilus; the outer GCL (oGCL) was defined as the half of the GCL adjacent to the molecular layer. A cell in the middle of the GCL was considered part of the subgranular zone; a cell bordering the GCL in the molecular layer was included in oGCL counts. The molecular layer was defined as the region between the superior limb of GCL and hippocampal fissure and between the inferior limb of the GCL and the inferior borders of the DG. The hilus included the superficial polymorphic layer. Counting was performed using 40× oil objective of a Nikon 90i fluorescent microscope equipped with Nikon C1 3-laser confocal system and a Nikon DS U1 digital camera. Using principles of unbiased stereology, the optical fractionator method was used to estimate cell counts for the DG (43). The total number of neurons (N) for each brain was estimated as: $N = \Sigma Q^- \times 1/tsf \times Vasf \times 1/ssf$, where tsf was the thickness sampling fraction, asf was the area sampling fraction, and ssf was the section sampling fraction. $\Sigma Q^-$ was the total number of cells actually counted in the dissectors that fell within the sectional profiles of the region of interest within sampled sections. All layers of the DG described previously were analyzed separately for cell counts. For each brain, at least 100 cells were counted based on coefficient of error determinations.

Hippocampi were homogenized to generate 10% (wt/vol) homogenate in buffer containing 50 mmol/L Tris-HCl (pH 7.4), 8.5% sucrose, 2 mmol/L EDTA, 2 mmol/L EGTA, 10 mmol/L β-mercaptoethanol, 5 mmol/L benzamidine, 0.5 mmol/L AEBSF, 4 μg/ml pepstatin A and 10 μg/ml each of aprotinin and leupeptin, 20 mmol/L β-glycerol phosphate, 100 mmol/L sodium fluoride, 1 mmol/L sodium vanadate, and 100 nmol/L okadaic acid. The protein concentration was measured by the modified Lowry assay (44). The tissues were then boiled in Laemmli sample buffer in a water bath for 5 minutes and subjected to 10% sodium dodecyl sulfate-polyacrylamide gel electrophoresis and Western blots. The blots were developed with rabbit monoclonal antibodies to CREB and phospho-CREB (1:1000; Cell Signaling Technology). Immunoreactive protein bands were visualized with chemiluminescence reagents (Thermo Scientific, Rockford, Ill.), and the films were scanned and analyzed using MultiGauge V3 software (Fuji Photo Film, Tokyo, Japan).

Statistical analyses were conducted with SASv5 (SAS Institute, Cary, N.C.). Data are presented as mean±SEM. For analysis involving multiple groups, analysis of variance (ANOVA) with post hoc Tukey or Fisher test were used. For all other comparisons (including intergroup comparisons), Student's t-test was used. Differences with $p < 0.05$ were considered significant. Data from 2N animals treated with vehicle or Peptide 6 were pooled because no significant differences were observed between these 2 groups.

Administration of the full-length CNTF protein in human clinical trials is known to cause anorexia, skeletal muscle loss, hyperalgesia, severe cramps, and muscle pain. Therefore, the physical state and general behavior of animals was carefully checked throughout the study period. There were no observed alterations in general physical state, including grooming, posture, and clasping reflex, due to either the genotype or the treatment with Peptide 6. Statistical analysis did not reveal any significant group effect or group × treatment effect in body weight (FIG. 3C; ANOVA, $p = 0.935$). Similarly, no differences of forepaw strength measured as fall latency in prehensile traction test (FIG. 3D; ANOVA, $p = 0.870$) or swim speed in the water maze (FIG. 3E; ANOVA, $p = 0.195$) were observed among groups. These data suggested that the genotype as well as the treatment with Peptide 6 did not induce any significant effect on general behavior.

The spatial reference memory task assesses hippocampal-dependent reference memory in rodents, requiring that mice use a spatial navigational strategy to find a fixed submerged escape platform. The hippocampal system processes information on the relationships among distal environmental cues into a spatial map where spatial coordinates of the submerged platform are encoded. The hippocampus is also crucial for memory storage, consolidation, and restitution of the spatial information.

Performance of animals during training was analyzed as latency to reach the submerged platform (FIG. 3F). Statistical analysis revealed a significant group effect (ANOVA, $p < 0.001$), suggesting significant difference of learning among groups. Post hoc analyses showed that wild-type mice displayed significantly better performance than Ts65Dn mice (Fisher test, $p < 0.001$). Separate analysis of learning for each group revealed that 2N animals and Ts65Dn mice treated with Peptide 6 significantly improved performance across days (ANOVA, $p < 0.007$), whereas Ts65Dn mice treated with vehicle only did not (ANOVA, $p = 0.175$). These results reflected that Ts65Dn mice presented a strong impairment of learning and that treatment with Peptide 6 alleviated this deficit albeit not restoring performance to control levels.

Analysis of the test for retention of learned information (probe trial) was conducted on the percentage of time animals spent in the target quadrant (FIG. 3G) and on the number of crossings of the platform zone (FIG. 3H). Ts65Dn mice neither preferentially visited the target quadrant compared with 2N mice (FIG. 3G; Student's t-test, p=0.007) nor crossed the platform zone (FIG. 3H; Student's t-test, p<0.001). These results confirmed the deficit of learning observed during the training of the task and showed compromised retention in Ts65Dn mice. Performance of Peptide 6Ytreated Ts65Dn mice was similar to that of 2N animals (FIG. 3G; Student's t-test, p=0.636; FIG. 3H; Student's t-test, p=0.121) and was significantly improved compared with vehicle-treated Ts65Dn mice (FIG. 3G; Student's t-test, p=0.024; FIG. 1H; Student's t-test, p=0.018). These results suggested that, although Ts65Dn mice treated with Peptide 6 did not display as good a performance as 2N animals did during the training, they encoded, stored, and/or remembered the spatial coordinates of the platform within the environment. Overall, these results showed that treatment with Peptide 6 rescued both learning and memory impairments of Ts65Dn mice.

As explained earlier, Peptide 6 was blood-brain barrier permeable and improved cognitive function of C57BL/6 normal adult mice as well as enhanced neuronal plasticity and neurogenesis through the CNTF pathway by inducing the inhibition of leukemia inhibitory factor. Because in the present study an alleviation of cognitive impairment was found by treatment with Peptide 6 in Ts65Dn mice, the effect of this peptide on neuronal plasticity and neural progenitor cell proliferation was investigated. The effect of treatment was analyzed with Peptide 6 on MAP2, PSD95, and GluR2/3 expression because an abnormal expression of these postsynaptic proteins that are critical for synaptic plasticity was previously reported in Ts65Dn mice.

Microtubule-associated protein 2 is a neuron-specific cytoskeletal protein involved in microtubule assembly and stabilization of dendritic shape, an essential step during neuron development and synaptic plasticity. A dramatic decrease of MAP2 immunoreactivity in the hippocampus of Ts65Dn mice was found versus 2N controls (FIG. 4A; Student's t-test, p=0.023). In Ts65Dn mice treated with Peptide 6, however, MAP2 immunoreactivity was significantly increased in the hippocampus (Student's t-test, p=0.047) and reached the control level (Student's t-test, p=0.439).

PSD95, a core structural postsynaptic protein critical for the tethering of AMPA-type glutamate receptors, plays a decisive role in controlling synapse strength and activity-dependent plasticity. A significant decrease of PSD95 immunoreactivity in the hippocampus of Ts65Dn was observed versus 2N mice (FIG. 4B; Student's t-test, p=0.010), and treatment with Peptide 6 increased PSD95 immunoreactivity to control level (Student's t-test, p=0.428).

GluR2/3 are selective AMPA receptors that play a functional role in hippocampal learning, mediating changes in synaptic strength that occurs after plasticity has been established by N-methyl-d-aspartate receptors. Analyses of GluR2/3 immunoreactivity showed a marked reduction in the hippocampi of Ts65Dn versus 2N mice (FIG. 4C; Student's t-test, p=0.023) and that treatment with Peptide 6 in Ts65Dn mice restored the GluR2/3 immunoreactivity (Student's t-test, p=0.010) to control level (Student's t-test, p=0.414).

The expression of Zif268 and pCREB immediate early genes reflects neuronal activity associated with the induction of plasticity underlying memory consolidation. Analysis of Zif268 by immunohistochemistry (FIG. 4D) and of CREB and pCREB by Western blots (FIG. 4E) after the water maze task revealed a general pattern of their reduction in the hippocampi of Ts65Dn mice that was alleviated by treatment with Peptide 6. Together, these findings on MAP2, PSD95, GluR2/3, and immediate early genes Zif268 and pCREB suggest a deficiency of neuronal plasticity in Ts65Dn mice that was rescued by long-term treatment with Peptide 6.

The number of BrdU-IR cells was dramatically decreased in the DG in Ts65Dn versus 2N mice (FIG. 5A, B; Student's t-test, p<0.001). In Peptide 6-treated Ts65Dn mice, the number of BrdU-IR cells was significantly increased compared with vehicle-treated Ts65Dn mice (Student's t-test, p=0.008) and not significantly different from 2N controls (Student's t-test, p>0.050). Analysis of BrdU-IR cells in the sublayers of the DG revealed that, in the inner GCL, there was that may cause abnormal connectivity. Statistical analysis conducted on the calculated index of ectopic birth (%) did not show any difference among groups (data not shown). These findings showed a reduction of proliferation of neural progenitor cells in Ts65Dn mice in the DG and that longterm treatment with Peptide 6 rescued this cell proliferation abnormality.

Down syndrome produces a variable set of clinical features, but mental retardation remains an invariable hallmark and the most invalidating aspect of the disease with a major impact on public health. The Ts65Dn trisomic mouse model exhibits a broad range of DS characteristics, including defects in synapse formation, neurophysiology and signaling pathways, neurogenesis deficit, and cognitive impairment. Accumulating evidence raises the exciting possibility that pharmacological regulation of neurotrophins can correct the homeostasis of the brain biochemical milieu. The present study shows for the first time that peripheral administration of Peptide 6 can shift the expression of dendritic and postsynaptic proteins MAP2, PSD95, and GluR2/3, as well as correct neuronal progenitor proliferation, and thereby rescue cognition in Ts65Dn mice. Our previous studies showed that Peptide 6, which corresponds to an active region of CNTF and is blood-brain barrier permeable, can enhance neurogenesis by antagonizing leukemia inhibitory factor. These findings suggested the therapeutic potential for Peptide 6 to correct impairments in neural cell proliferation and synaptic plasticity and consequent cognitive deficits in Ts65Dn mice. Previous studies showed that long-term treatment with memantine or estrogen replacement therapy alleviated cognitive impairment in Ts65Dn mice and increased levels of neurotrophins. On the other hand, it has been shown that treatment of Ts65Dn mice with fluoxetine or lithium increased neurogenesis.

In the present study, treatment with Peptide 6 did not induce weight loss, modification of general behavior, or any other apparent deleterious adverse effects. This observation is crucial because administration of CNTF induced serious adverse effects including anorexia, skeletal muscle loss, hyperalgesia, cramps, and muscle pain in clinical trials, and antibodies to CNTF were detected in the plasma of the treated individuals.

In the spatial reference memory task, the hippocampus is crucial for processing information on relationships among distal environmental cues into a spatial map and is also essential for memory storage, consolidation, and restitution of the spatial information. It was observed that, in Ts65Dn mice, learning and memory performances were dramatically impaired compared with 2N controls. These results are in agreement with previous studies and show that trisomic animals were not able to encode, store, and/or recognize spatial representation of the environment and coordinates of the submerged platform. Long-term treatment with Peptide 6 alleviated these deficits. Along with the improvement of spatial learning capabilities, it was observed that treatment with Peptide 6 also alleviated spatial memory, increasing Ts65Dn mice's performance to control levels in the probe trial. These results suggested that treatment with Peptide 6 enhanced memory consolidation mechanisms.

Synaptic plasticity, or the long-lasting alterations in the efficacy of synaptic connections between 2 neurons, is thought to be the cellular substrate of memory. It is now widely reported that cognitive deficits in Ts65Dn mice are strongly associated with alterations in the structure of dendritic spines in the hippocampus and the cortex, failure of long-term potentiation in the hippocampus and fascia dentate, and abnormal expression of synaptic proteins in the hippocampus. In the present example, it was found that treatment with Peptide 6 positively regulated MAP2, PSD95, and GluR2/3 AMPA receptor expression in the hippocampus of Ts65Dn mice. These proteins are critically involved in the glutamate excitatory pathway of long-term synaptic plasticity and long-term memory. Glutamate regulation of MAP2 phosphorylation transduces neural activity into modifications in dendritic structure. PSD95 anchors AMPA-type glutamate receptors and participates in AMPA receptor delivery during experience-driven plasticity and long-term potentiation. AMPA receptors play a functional role in hippocampal learning, mediating changes in synaptic strength that occurs after plasticity has been established by N-methyl-D-aspartate receptors. Together, the results suggest that Peptide 6 can regulate expression of postsynaptic proteins playing central role for synaptic strengthening induced by experience-driven plasticity.

Immediate early genes, and more specifically Zif268 and CREB, are considered markers of neuronal activity associated with the induction of plasticity underlying memory consolidation. It was observed that the level of expression of these proteins induced by a cognitive stimulation tends to decrease in Ts65Dn mice but that treatment with Peptide 6 restored Zif268 and pCREB after cognitive stimulation to control levels. These observations therefore confirmed the beneficial effect of treatment with Peptide 6 in Ts65Dn mice, alleviating learning and memory impairments and thus might be driven by enhancing neuronal plasticity.

In addition to weakness of synaptic plasticity, several studies report severe neuronal proliferation impairment in the dentate gyrus of neonate and adult Ts65Dn mice. Because this neurogenesis impairment is reported as early as embryonic stages in Ts65Dn mice, such altered embryonic brain development may underlie postnatal defects. Consistent with these studies, a dramatic decrease of BrdU-IR cells was observed in the dentate gyrus of Ts65Dn mice that was rescued by Peptide 6. It is now widely reported that neurogenesis is vulnerable to pathologic conditions, resulting in a decline in the ability of neurons to modify their connectivity in response to environmental and physiological stimuli contributing to reduction in memory function. Imbalances of neurotrophins have dramatic repercussions on proliferation of neural progenitor cells, whereas exogenous addition of growth factors such as insulin-like growth factor 1, epidermal growth factor, and fibroblast growth factor or a reduction of corticosteroid levels by adrenalectomy can, at least partially, restore the rate of neural stem cell proliferation. Therefore, it is reasonable to speculate that enriching the brain biochemical milieu can trigger appropriate signals for neurogenesis.

Individuals with DS develop Alzheimer disease histopathology in their fourth decade of life in 100% of cases. In Ts65Dn mice, an increase of amyloid precursor protein levels without increase of $A\beta1-40$ and $A\beta1-42$ was reported from 10 months of age, as well as clusters of extracellular granules that are positive for tau and reelin. In a related study, it was reported that Peptide 6 did not have any significant effect on moderate stages of $A\beta$ and tau pathologies in a 3xTg-AD mouse model of Alzheimer disease. Therefore, a beneficial effect of treatment with Peptide 6 is unlikely to be due to the reduction of $A\beta$ and tau pathologies in Ts65Dn mice.

In conclusion, long-term treatment with Peptide 6 rescued the commonly described features of Ts65Dn mice, including learning and memory deficits, failure of hippocampal synaptic plasticity, and impairment of neurogenesis. Peptide 6 treatment enhanced memory consolidation, acted on proteins that are critically involved in strengthening of synaptic plasticity, and increased the pool of neurons potentially recruited into the network of information processing by promoting neuronal precursor proliferation.

EXAMPLE 3

All in vivo studies for characterization of peptides (stereology and behavioral analysis) were performed on 8-10-month-old female retired breeders of C57B16 background. The animals were acclimatized for at least 3 weeks to exclude occasional pregnant mice from the studies. Mice were group-housed (3 animals per cage) with a 12:12 light:dark cycle and with free access to food and water. All procedures were conducted in accordance with approved protocols from our institutional Animal Welfare Committee.

Based on Peptide 6, a set of four tetrapeptides with overlapping residues to the sequence of the parent peptide CNTF 6 (see Table 3) was further constructed. These peptides, CNTF 6a-d, were synthesized on a commercial basis by the Pan Biotechnology Facility of Stanford University (Palo Alto, Calif.).

TABLE 3

| CNTF Peptide | Position in CNTF |
| --- | --- |
| Peptide 6a | 145-148 |
| Peptide 6b | 146-149 |
| Peptide 6c | 147-150 |
| Peptide 6d | 148-151 |

To study neurogenesis, mice received subcutaneous implants of extended release depot pellets containing either CNTF peptides 6a or 6c for 30 days of continuous dosing (Innovative Research of America, Sarasota, Fla.). For control groups, the pellets consisted of the carrier biopolymer only. For implantation, the mice were anesthetized with 2.5% Avertin (0.38 ml for a 25 g animal). Under sterile conditions, the pellets were then subcutaneously implanted along the anterolateral aspect of the right shoulder with a precision trochar (Innovative Research of America). The animals were then transferred to the animal colony after recovery from anesthesia. There were no complications associated with the implantation and treatment. BrdU was given as two daily i.p. injections (100 mg/kg/dose) for five days starting on day 2 of peptide treatment. Neurogenesis was assessed in the dentate gyrus (DG) by counting the number of BrdU-immunoreactive (BrdU-IR), BrdU-DCX-IR and BrdU-NeuN-IR cells in various layers of the DG. Employing principles of unbiased stereology, the optical fractionator method was used to estimate cell counts for the DG.

The following primary antibodies were used for immunohistochemistry: anti-BrdU (1:400; Accurate) a rat monoclonal raised against BrdU; anti-DCX (1:200; Santa Cruz Biotechnology Inc.), a goat polyclonal antibody raised against an 18-amino acid peptide representing residues 384-410 of human doublecortin; anti-NeuN (1:500; Chemicon), a mouse monoclonal antibody raised against purified cell nuclei from mouse brain; Anti-c-Fos (Ab-5) (1:500; Calbiochem), a rabbit polyclonal antibody raised against a synthetic peptide corresponding to amino-acids 4-17 of human c-Fos; SMI52 (1:1000; Sternberger Monoclonals), a mouse monoclonal antibody specific for the mature neuronal marker MAP2a,b; antisynaptophysin, SYN (1:200; Chemicon), a mouse monoclonal antibody raised against vesicular fraction of bovine brain. The following secondary antibodies were used: Alexa 488-conjugated goat anti-mouse IgG antibody and Alexa 594-conjugated goat anti-rabbit or anti-rat IgG antibody (Molecular Probes); biotinylated anti-rat IgG antibody and Cy5-conjugated goat anti-mouse antibody (Jackson ImmunoResearch).

At the end of treatment, all animals were anesthetized with an overdose of sodium pentobarbital and transcardially perfused with 0.1 M PBS. After perfusion, the brains were removed from the skull, the left hemisphere was immediately frozen for future biochemical analysis and the right hemisphere was fixed in 4% paraformaldehyde in 0.1 M PBS for at least 24 hours at room temperature. Tissues were then stored in 30% sucrose solutions at 4° C. until sectioning. The brains were sectioned sagittaly on a freezing sliding microtome at 40 pm through the entire hippocampus and the sections were stored in glycol anti-freeze solution (Ethylene glycol, glycerol and 0.1 M PBS in 3:3:4 ratio) at −20° C. till further processing.

Immunohistochemistry was performed as described elsewhere (Kuhn et al., J. Neurosci 17 (15) (1997): 5820-5829). Briefly, every 5th brain section was chosen for quantification of cell number and every 10" section was chosen for staining intensity scanning. Immunohistochemistry was performed on free floating sections. For BrdU immunohistochemistry, epitope retrieval and staining were performed as previously described (Kuhn et al., J. Neurosci 17 (15) (1997): 5820-5829).

Neurogenesis was assessed in the DG by counting the number of BrdU-immunoreactive (BrdU-IR), BrdU-DCX-IR and BrdU-NeuN-IR cells in various layers of the DG. The granule cell layer (GCL) was subdivided into an inner and outer half (iGCL and oGCL). The iGCL consisted of the subgranular zone (SGZ, defined as a 2-3 nuclei thick layer bordering the GCL) and the inner half of the GCL adjacent to the Hilus (Hil); the outer GCL (oGCL) was defined as the half of the GCL adjacent to the Molecular layer (Mol). A cell in the middle of the GCL was considered part of the iGCL and a cell bordering the GCL in the Mol was included in oGCL counts. Mol was defined as the region between the superior limb of GCL and hippocampal fissure and between the inferior limb of the GCL and the inferior borders of the DG. Hil included the superficial polymorphic layer.

All sections were collected using the random uniform sampling scheme. For BrdU-IR cells, counting was performed on every 5th section using 40× oil objective of a Nikon 90i fluorescent microscope equipped with Nikon C1 three laser confocal system and a Nikon DS U1 digital camera. Employing principles of unbiased stereology, the optical fractionator method was used to estimate cell counts for the DG (West et al., Anat Rec 231 (1991): 482-497). All layers of the DG described above were analyzed separately for cell counting. For each brain, at least 100 cells were counted based on coefficient of error determinations.

For BrdU-DCX-, BrdU-NeuN-, and c-Fos-NeuN-IR cells, only GCL (consisting of iGCL and oGLC described above) was counted using 100× oil objective in every 10th section. To ensure objectivity, z stacks were collected for each double IR cell and analyzed later by generating maximum projection and 3D constructs. A cell was counted only when it showed double IR on 3D reconstructed images.

For MAP2 and Synaptophysin IR, the entire area of GCL was outlined on every 10th section. Maximum projection images were then generated based on confocal z stacks, and the antibody staining was quantitated by measuring mean pixel intensity (MPI) with the help of Image-Pro Plus 5.0 software (Media Cybernetics).

All quantitations based on immunohistochemistry were verified independently on coded slides by a second investigator.

For behavioral studies, performance on the Morris Water Maze task was assessed in three groups of 10 mice each (placebo, CNTF6a and CNTF6c) which received peptide treatment for 30 days. To avoid daily stress due to injections, all animals undergoing behavioral studies received subcutaneous implants of CNTF 6a, CNTF 6c or placebo pellets as described above.

All animals for behavioral testing were coded such that the experimentator was blind to the assignment of the animals to specific treatment groups. The Morris Water Maze procedure was performed using a 110 cm diameter circular tank. Before training, the mice were handled gently for 2-3 min/day during 3 days to minimize non-specific stress. Acquisition was started with the submerged (invisible) escape platform in the North-East quadrant and each animal was given 60 sec to find the submerged escape platform. If the mouse did not find the platform in 60 sec, it was guided to it. Five such acquisition trials were given on each day, for four consecutive days. A test for retention, or probe trial, was given 24 hours later. During the probe trial the mouse was allowed to swim in the tank without the escape platform for 60 seconds. This was followed by second and third probe trials 15 and 30 days from the first probe trial. Each probe trial was immediately followed by a "retraining session" consisting of 5 trials/animal to consolidate learned behavior.

The measures of learning were the time and distance swum to reach the escape platform. For retention during the probe trial, the tank was divided into four imaginary quadrants and a small zone where the escape platform had been (virtual platform). The measures of retention were the percent of time spent and the percent of distance swum in each quadrant, and the number of entries into the platform zone.

Mouse behavior in the Morris Water Maze was monitored by a Samsung Digital Camera (SDC 4304) mounted to the ceiling and tracked and timed by a SMART (Pan Lab/San Diego Instruments) version 2.0.14 software.

Data are represented as mean±SEM. For analysis involving multiple groups, ANOVA with post hoc Tukey's test was used. For analysis of data with skewed distributions, the non-parametric Mann-Whitney U-test was used. For all other comparisons (including inter-group comparisons), Student's t-test was used. Differences with p<0.05 were considered significant.

The four CNTF tetrapeptides were initially screened in a behavioral paradigm employing the Morris Water Maze. Two CNTF tetrapeptides, CNTF 6a and CNTF 6c, were chosen for detailed stereological and behavioral analysis.

Fifteen mice were divided into 3 groups including placebo, CNTF 6a and CNTF 6c. Mice received subcutaneous implants of 30-day extended release pellets containing either CNTF 6a or CNTF 6c (50 nmol/peptide/animal/day, n=5/group) or placebo (n=5). Referring to FIG. 6(a), dividing cells were labeled with BrdU given i.p. for five days, twice a day (100 mg/kg/animals/dose). Compared to the placebo group, CNTF 6c increased BrdU-immunoreactive (BrdU-IR) cell counts in the GCL by 31% (p<0.05, Student's t-test). CNTF 6a had not significant effect on cell proliferation in the GCL, as seen in FIGS. 6(b) and 6(c) and Table 2.

Figure 6:
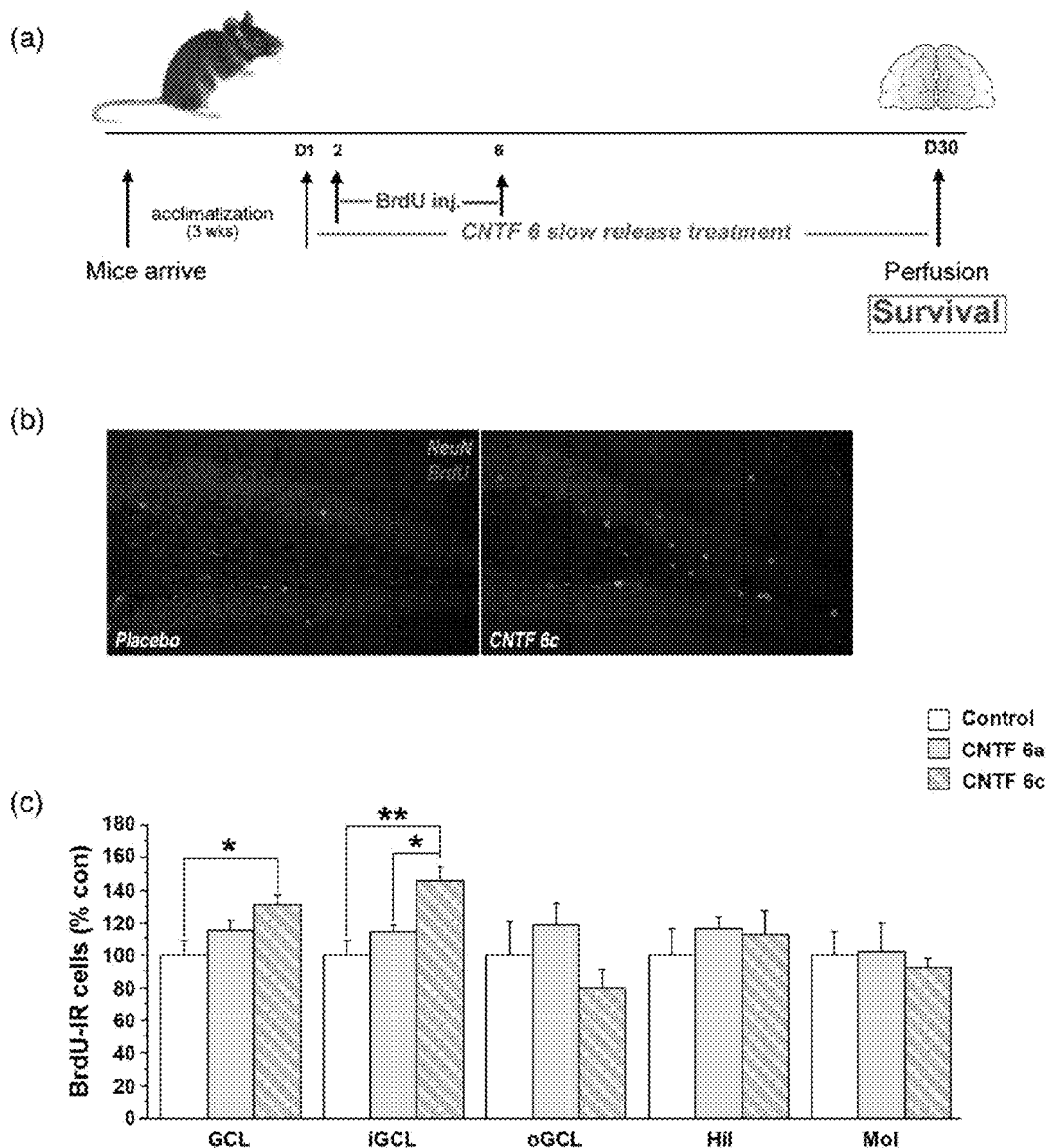

Further examination of the proliferation in four sub-regions of the hippocampus (for anatomical definitions, see "Materials and Methods" section): iGCL (inner granule cell layer, which included the SGZ), oGCL (outer granule cell layer, Mol (molecular layer) and Hil (hilus), revealed that compared to control group, CNTF 6c increased the number of BrdU-IR cells in the iGCL by 45% (p<0.001, Student's t-test), whereas no significant differences were observed in either oGCL, Mol or Hil, see FIGS. 6(*b*) and 6(*c*), and Table 4. CNTF 6a had no effect on BrdU-IR cell numbers in either of the four sub-regions of the DG. Together, these data suggest that both CNTF 6c increased BrdU-IR cells in the DG and this increase was mainly confided to the iGCL, the neurogenic niche of the hippocampus.

TABLE 4

Stereological counts (±SEM) of BrdU-IR cells in various subregions of the hippocampus in 30-day treated mice (n = 5/group)

|  | GCL | iGCL | oGCL | Mol | Hil |
|---|---|---|---|---|---|
| Control | 427 ± 38 | 334 ± 28 | 93 ± 19 | 526 ± 77 | 108 ± 17 |
| CNTF 6a | 493 ± 28 | 382 ± 15 | 110 ± 13 | 538 ± 99 | 126 ± 8 |
| CNTF 6c | 560 ± 24 | 486 ± 31 | 74 ± 10 | 487 ± 28 | 121 ± 16 |

$p < 0.05$, $p < 0.01$ Student's t-test

Doublecortin (DCX), an immature neuronal marker, is used to quantitate early neuronal fate determination in DG progenitors. The number of DCX-IR cells in the GCL (iGCL+oGCL) was quantitated at the time of perfusion, a snapshot-quantitation of immature neurons in response to 30-day treatment with CNTF tetrapeptides, as seen in FIG. 7(*a*). Stereological analysis revealed that compared to the placebo, CNTF 6c treatment increased DCX-IR cells in the GCL by almost 2 folds (~91%, increase, p<0.001, Student's t-test), whereas CNTF 6a treatment did not show any significant difference as seen in FIG. 7(*a*) and Table 5). These data suggest that at the time of perfusion, there were more immature neurons in the GCL of CNTF 6c treated animals. Whether this also reflects early neuronal differentiation of dividing progenitors cannot be determined by our study.

TABLE 5

Stereological counts (±SEM) of cells expressing various neuronal maturity and/or activity markers in the granule cell layer of the dentate gyrus in 30-day treated mice (n = 5/group)

|  | DCX | NeuN-BrdU/BrdU | c-fos-NeuN |
|---|---|---|---|
| Control | 306 ± 72 | 24 ± 2 | 168 ± 17 |
| CNTF 6a | 360 ± 33 | 19 ± 2 | 214 ± 27 |
| CNTF 6c | 656 ± 43 | 39 ± 2 | 247 ± 23 |

$p < 0.05$, $p < 0.01$ Student's t-test

Net neurogenesis in the DG is determined by the number of progenitors which survive as mature neurons, as more than half of the progenitors either die as stem cells or as immature precursors (eg. DCX-IR cells). In order to determine whether CNTF 6c induced differentiation of DG progenitors into mature neurons, the number of BrdU-IR cells expressing the mature neuronal marker NeuN in the GCL of the DG was counted. A 62% increase in BrdU-NeuN-IR cells in CNTF 6c treated animals was found when compared with the placebo group, whereas CNTF 6a treatment had no effect (p<0.01, Stundent's t-test; FIG. 7(*b*) and Table 5).

For neurogenesis to have physiological significance, newly born neurons need to be functionally integrated into the hippocampal circuitry. Neuronal activity, an indication of functional integration, can be indirectly quantitated by studying changes in the expression of immediate-early genes like c-fos and zif. Towards that aim, it was investigated whether CNTF 6c induced an increase in c-fos protein expression, providing a biological substrate for neuronal firing, and ultimately spatial encoding. Stereological counts of c-fos expressing mature DG neurons without behavioral stimulation, i.e. at basal levels reflecting activity in the cage (FIG. 8(*a*) and Table 5) were compared. It was found a ~47% increase in the number of mature neurons (NeuN-IR) co-expressing c-fos in the GCL in CNTF 6c treated mice (p<0.05, Student's t-test). There was also evidence of increased neuronal activity in newly born mature neurons as some BrdU-NeuN-IR cells in the GCL also co-expressed zif, as seen in FIG. 8(*a*).

Microenvironment within the brain undergoes significant changes in both aging and disease. The rate of neurogenesis and synaptogenesis in the brain indirectly reflect its microenvironment. In order to study whether CNTF 6c-induced enhancement of DG nerogenesis was also accompanied by changes in local neurothrophy, the expression of MAP2 and synaptophysin, indicators of dendritic arborization and synaptic activity respectively, in the GCL of treated animals was measured. An increase in both indicators of neurotrophy (31% and 26% respectively, p<0.01, Student's t-test) as measured by mean-pixel intensity was found, as seen in FIG. 8(*b*).

Increased neuronal differentiation of DG progenitors, enhanced neuronal firing, upregulated synaptogenesis and neurothrophy are all key biological substrates of memory processing within the DG. Therefore, it was evaluated whether CNTF 6c treatment also had an effect on the cognitive function of treated animals. Since normal adult mice were used as experimental animals, it was crucial not to miss any effect on memory acquisition and learning that the 30-day peptide treatment might have had. Therefore, a partial training paradigm was used to evaluate learning and memory in the Morris Water Maze. Treated mice were trained on the Morris Water Maze for a total of 20 sessions spanning 4 days after which they were subjected to the first probe trial (P1). Two additional probe trials (P2 and P3) were administered 15 and 30 days after P1. Each probe trial was immediately followed by 4 retraining sessions to allow memory consolidation, as seen in FIG. 9(*a*). Learning was evaluated in terms of latency and distance traveled to reach the invisible escape platform. Retention was measured on probe trials by the percent of time and travel distance in the target quadrant, and the number of crossings of the virtual platform.

Animals in all three groups learned well as evident by declining swim latencies to reach the submerged platform, as seen in FIG. 9(*a*). However, there was no effect of either CNTF 6a or CNTF 6c treatment on learning in the spatial reference memory task (two way ANOVA, p=0.667).

Analysis of retention on the three probe trials showed no effect of the treatment on P1, whereas P2 and P3 showed significant differences in both measures of retention in CNTF 6c treated mice. Analysis of time spent in the target quadrant across three probe trials indicated that whereas all animals spent equal amount of time on P1, both placebo and CNTF 6a treated animals reduced this time during subsequent P2 and P3. CNTF 6c-treated animals however, spent the same percent amount of time in the target quadrant during the three probe trials, indicating better preservation of the memory trace in these mice, as seen in FIG. 9(*b*). Analysis of the percent distance traveled within the target quadrant also presented a similar picture for CNTF 6c across the three probe trials, as seen in FIG. 9(*c*).

EXAMPLE 4

In the foregoing Examples it was shown that an 11-mer peptide, Peptide 6 (Ac-VGDGGLFEKKL-NH$_2$) and a subsequence of it, Peptide 6c (Ac-DGGL-NH$_2$), enhanced hippocampus dependent learning and memory, increased neurogenesis and neuronal plasticity in normal adult mice. Although peptides in general are readily bioavailable, systemic degradation through proteases and relatively poor blood-brain-barrier (BBB) permeability pose challenges in rendering peptides "druggable." To address these design goals, adamantane building blocks were added to the C-terminus or both C- and N-termini of Peptide 6c. These bulky, highly lipophilic tricyclic alkane building blocks can increase the BBB permeability of peptides and block enzymatic degradation through exopeptidases. In the present example, it could be shown that when administered peripherally to normal adult mice, the pentamer Ac-DGGL$^A$G-NH$_2$, called P21, significantly enhanced cognition, increased proliferation and differentiation of adult hippocampal progenitors and promoted the expression of synaptic vesicle proteins, synaptophysin and synapsin I.

FIG. 10 shows the design and structures of peptidergic compounds employed in this example. For synthesis of peptidergic compounds incorporating adamantane building blocks, compounds P21 (Ac-DGGL$^A$G-NH$_2$) and P22 (1-Ad-CO-DGGL$^A$G-NH$_2$), animals and housing, one trial object recognition test, spatial reference memory task in the water maze, immunohistochemistry, cell counts by stereology, analysis of the mechanism of action of P21 through LIF receptor in HepG2 cells, and statistical analysis.

Peptidergic compounds Ac-DGGL$^A$G-NH$_2$ (P21) and 1-Ad-CO-DGGL$^A$G-NH, (P22) (FIG. 10) were synthesized by standard solid phase peptide synthesis (SPPS) methods following the Fmoc-strategy. 3-(9-Florenylmethoxycarbonyl)aminoadamantane-1-carboxylic acid (Fmoc-$^A$Gly) was synthesized as described previously (Wanka, L., et al. Eur J Org Chem 9 (2007): 1474-1490). Fmoc-a-amino acids, activation reagents and other chemicals used were purchased from EMD Chemicals (Gibbstown, USA) and used as supplied. Solvents used were peptide synthesis grade. Manual SPPS was performed on Rink amide AM resin (200-400 mesh, Novabiochem) in a peptide synthesis vessel. Loading (2×1 h) as well as chain elongation (2×45 min) were performed via double-couplings using 2×3 equivalents (over resin substitution) of the respective Fmoc-amino acid, 2-(1HBenzotriazole-1-yl)-1,1,3,3-tetramethylaminium hexafluorophosphate (HBTU), and 1-Hydroxybenzotriazole (HOBt), and 2×6 equivalents of N,N-diisopropylethlamine (DIPEA). Acetylation was performed using 10 equivalents of acetic anhydride and DIPEA over resin loading for 30 min Adamantanoylation was performed using adamantane-1-carboxylic acid (Acros Organics, Belgium) in a double-coupling procedure with HBTU/HOBt activation as described above for the chain elongation steps. Removal of the temporary Fmoc-protective group was performed using 20% piperidine in N,N-dimethylformamide (DMF, 2×20 min). After each chain elongation and Fmoc-cleavage step, the resin was washed with DMF (5×1 min), dichloromethane (DCM, 5×1 min), and DMF (3×1 min). The peptides were cleaved from the resin with trifluoroacetic acid (TFA)/water/triisopropylsilane (95:2.5:2.5) for 3 h and precipitated by the addition of ice-cold diethyl ether. They were collected by centrifugation. The crude precipitates were resuspended in fresh ice-cold diethyl ether and centrifuged another two times. After dissolving in water/acetic acid (2:1) and extraction with diethyl ether/hexanes (1:1), the aqueous solution of the crude peptides was lyophilized. The peptides were purified by semi-preparative reversed-phase HPLC using a Waters DeltaPak RP18 column (19×300 mm, 5 nm, 300 Å) and gradients of solvent B in solvent A (A: water, 0.1% TFA; B: acetonitrile, 0.1% TFA) at 5 mL/min flow rate. Product fractions were analyzed by analytical HPLC using an Agilent Zorbax Eclipse XDB-C8 column (4.6×150 mm), and linear gradients of solvent B in solvent A at 1 mL/min flow. Both analytical and semipreparative HPLC were monitored at 220 nm using a variable wavelength detector. Product fractions containing the peptides in >95% purity as analyzed by analytical HPLC were pooled, lyophilized and used for the present study. Proton NMR spectra were recorded on a Varian 600 spectrometer. Proton chemical shifts are reported in ppm (δ) relative to internal tetramethylsilane (TMS, δ 0.0 ppm).

Data are reported as follows: chemical shift (multiplicity [singlet (s), doublet (d), triplet (t), quartet (q), multiplet (m)], coupling constants [Hz], integration). The spectra were obtained at 25° C. ESI-MS spectra were recorded on an Agilent 1100 series MSD instrument.

The HPLC and NMR data of P21 and P22 are as follows:

Ac-DGGL$^A$G-NH2 (P21) (SEQ ID NO:18): Preparative HPLC: 15-45% solvent B in solvent A in 80 min, product fractions eluted at 40-43 min Analytical HPLC: 10-60% solvent B in solvent A in 20 min, rt=9.5 min 1H-NMR (600 MHz, [D6]DMSO): δ=0.83 (d, J=6.5 Hz, 3H, Leu-Hδ); 0.87 (d, J=6.6 Hz, 3H, Leu-Hδ); 1.36-1.47 (m, 2H, Leu-Hβ); 1.49-1.59 (m, 3H, Leu-Hγ and adamantane-CH$_2$); 1.62-1.71 (m, 4H, 2× adamantane-CH$_2$); 1.79-1.90 (m, 4H, 2× adamantane-CH$_2$); 1.86 (s, 3H, acetyl-CH$_3$); 1.92 (br. s, 2H, adamantane-CH$_2$); 2.06-2.12 (m, 2H, 2× adamantane-CH); 2.70 (dd, J=16.6 and 5.4 Hz, 1H, Asp-Hβ); 3.66-3.75 (m, 5H, 4×Gly-Hα and Asp-Hβ); 4.21-4.27 (m, 1H, Leu-Hα); 4.51-4.57 (m, 1H, Asp-Hα); 6.71 (s, 1H, CONH$_2$); 6.98 (s, 1H, CONH$_2$); 7.36 (br. s, 1H, $^A$Gly-NH); 7.69 (d, J=8.4 Hz, 1H, Leu-NH); 7.99 (t, J=5.9 Hz, 1H, Gly-NH); 8.20 (t, J=5.7 Hz, 1H, Gly-NH); 8.24 (t, J=7.6 Hz, 1H, Asp-NH); 12.32 (br. s, 1H, Asp-CO$_2$H). MS (ESI): m/z=579.4 [M+H]$^+$ (calcd. 579.3).

1-AdCO-DGGL$^A$G-NH$_2$ (P22): Preparative HPLC: 10-43% solvent B in solvent A in 79 min, then 43-60% solvent B in solvent A in 10 min, then 20 min at 60% solvent B in solvent A. Product fractions eluted at 83-86 min Analytical HPLC: 10-60% B in A in 20 min, rt=15.5 min 1H-NMR (600 MHz, [D6]DMSO): δ=0.82 (d, J=6.8 Hz, 3H, Leu-Hδ); 0.87 (d, J=6.8 Hz, 3H, Leu-Hδ); 1.35-1.45 (m, 2H, Leu-Hβ); 1.49-1.59 (m, 3H, Leu-Hγ and adamantane-CH$_2$); 1.61-1.70 (m, 10H, 5× adamantane-CH$_2$); 1.75-1.80 (m, 6H, 3× adamantane-CH$_2$); 1.80-1.89 (m, 4H, 2× adamantane-CH$_2$); 1.92 (br. s, 2H, adamantane-CH$_2$); 1.94-1.98 (m, 3H, 3× adamantane-CH); 2.04-2.11 (m, 2H, 2× adamantane-CH); 2.56 (dd, J=16.0 and 8.0 Hz, 1H, Asp-Hβ); 2.74 (dd, J=16.1 and 5.5 Hz, 1H, Asp-Hβ); 3.66-3.75 (m, 4H, 4×Gly-Hα); 4.21-4.27 (m, 1H, Leu-Hα); 4.53-4.58 (m, 1H, Asp-Hα); 6.71 (s, 1H, CONH$_2$); 6.98 (s, 1H, CONH$_2$); 7.35 1H, $^A$Gly-NH); 7.62 (d, J=7.7 Hz, 1H, Leu-NH); 7.71 (d, J=8.5 Hz, 1H, Asp-NH); 7.88 (t, J=5.5 Hz, 1H, Gly-NH); 8.03 J=5.9 Hz, 1H, Gly-NH); 12.20 (br. s, 1H, Asp-CO$_2$H). MS (ESI): m/z=699.4 [M+H]$^+$ (calcd. 699.4).

All in vivo studies for characterization of compounds (stereology and behavioral analysis) were performed on 8-10-month-old female retired breeders of C57B16 background. Animals were acclimatized for at least 3 weeks to exclude occasional pregnant mice from the studies. Mice were group-housed (3 animals per cage) with a 12:12 hours light/dark cycle and with free access to food and water.

For the compound treatment, mice (8 animals/group) received subcutaneous implants of extended release depot pellets containing P21 or P22 at 25 nmol/day for 35 days of continuous dosing (Innovative Research of America, USA). For the control group (8 animals), pellets consisted of the carrier polymer only. Mice were anesthetized with 2.5% Avertin (0.38 ml for a 25 g animal). Under sterile conditions, pellets were implanted subcutaneously along the anterolateral aspect of the right shoulder with a precision trochar (Innovative Research of America). After recovery of anesthesia, animals were transferred to the animal colony. No complications associated with the implantation and treatment were observed. All procedures on animals were conducted in accordance with approved protocols from our Institutional Animal Welfare Committee.

To investigate neurogenesis, BrdU (Sigma, USA) was given as two daily i.p. injections (100 mg/kg/dose) for five days starting on day 2 of compounds treatment.

The physical state and condition of animals were carefully monitored throughout the treatment by evaluating grooming, physical state and clasping reflex. Body weight was also recorded.

In the one-trial object recognition task, animals are exposed to two different objects which they have to identify as novel or familiar based on the memory of an earlier experience with one of the two objects they encountered in the same open field. The familiar object is explored shorter than the novel encountered one because the representation of the former is still available in memory. The one-trial object recognition task tests some aspects of episodic memory but is limited to memory of an object (what), the location of an object (where), and the context in which it was encountered (which). However, the temporal dimension of the episode remains inaccessible to the experimenter, and because of this reason this task in animals is considered a test of short term memory.

The testing apparatus was a classic open field (i.e. a PVC square arena, 50×50 cm, with walls 40 cm high). The open field was placed in a part of the room separated from the experimenter with a black opaque curtain. The open field was surmounted by a video camera connected to a computer. Three objects were employed in this task. The general procedure consisted of three different phases: a familiarization phase (1 session of 20 min), a sample phase, and a test phase. On the first days, mice were individually submitted to the familiarization session during which they were introduced in the empty arena in order to become familiar with the apparatus. This familiarization session allowed to record a baseline level of locomotor activity (measuring the distance covered in the open field) and of anxiety (measuring the time the animals spent in the centre of the arena during the first five minutes). On the second day each mouse was first submitted to the sample phase (session 1, ten minutes) for which two identical objects were placed in a symmetric position from the centre of the arena. After a 15 minute delay during which the mouse returned to its home cage, it was reintroduced in the arena to perform the test phase (session 2, 10 min). The mouse was then exposed to two objects: a familiar object (previously presented during the sample phase) and a new object, placed at the same location as during the sample phase. Data collection was performed using a video tracking system (Smart version 2.0.14 software. Pan Lab/San Diego Instruments).

Object discrimination was calculated as follows: OD= (time spent close to new object)/(time spent close to new object)+(time spent close to old object)×100.

Spatial reference learning and memory were evaluated in the water maze using a procedure adapted from that previously described by Morris et al. (Morris, R. G., et al. Nature 297 (1982): 681-3). The test required that mice used a spatial navigational strategy based on a spatial representation of the environment to find a fixed submerged escape platform. The procedure was performed in a 180 cm diameter circular tank. The pool was filled with water ($21\pm1°$ C.) made opaque by adding white non-toxic paint. Acquisition started with the escape platform (15 cm diameter submerged 1 cm below water surface) in the Northwest quadrant and each animal was given 90 seconds to find the platform. If the mouse did not find the platform in 90 seconds, it was gently guided to it. At the end of each trial, the mouse was left on the platform for 20 seconds, then dried and returned to its home cage until the next trial. Five such acquisition trials were given on each day for four consecutive days. A test for retention, or probe trial (PT), was given 24 hours later. During the probe trial the mouse was allowed to swim in the tank without the escape platform for 60 seconds. This was followed by second and third probe trials 15 and 30 days after the first probe trial.

The measures of learning were the time and distance covered to reach the escape platform. For the probe trial, the tank was divided into four imaginary quadrants and a small zone where the escape platform had been. The measure of retention was calculated as the ratio of time spent or distance covered in target quadrant over that in the three other quadrants.

Mouse behavior in the water maze was monitored by a Samsung Digital Camera (SDC 4304) mounted to the ceiling and tracked and timed by a SMART (Pan Lab/San Diego Instruments) version 2.0.14 software.

At the end of the behavioral experiment, animals were anesthetized with an overdose of sodium pentobarbital (120 mg/kg) and transcardially perfused with 0.1 M phosphate buffered saline (PBS). After perfusion, the brains were removed from the skull, the left hemisphere was immediately frozen for future biochemical analysis and the right hemisphere was immersion fixed in 4% paraformaldehyde in 0.1 M PBS for at least 24 hours at room temperature. Tissues were equilibrated and stored in 30% sucrose solution at 4° C. until sectioning. The brains were sectioned sagittaly on a freezing sliding microtome at 40 nm through the entire hippocampus and the sections were stored in glycol anti-freeze solution (Ethylene glycol, glycerol and 0.1 M PBS in 3:3:4 ratio) at −20° C. until further processing.

For double labeling of BrdU and NeuN, brain sections were pretreated with 2 M HCl at 37° C. for 30 min and neutralized with 0.1 M borate buffer (pH 8.5) for 10 minutes. Tissue sections were incubated first for 30 min with blocking buffer (4% normal goat serum+0.1% Tween-20 in PBS) and then overnight at 4° C. in the presence of BrdU (Millipore Corporation, USA) and NeuN (Millipore Corporation) antibodies diluted 1:400 and 1:100, respectively. To determine the integrity of presynaptic terminals, tissues were labeled with anti-synaptophysin (1:200; Clone SY38, Millipore Corporation) or anti-synapsin I (1:200; Stressgen Biotechnologies Corporation, Canada). The brain sections were incubated in primary antibody over night at 4° C., respectively. Alexa 488 and 594 (1:500; Invitrogen, USA) were used as secondary antibodies. All images were obtained using Nikon Eclipse 90i and D-Eclipse C1 microscopes (Nikon Corporation, Japan).

Neurogenesis in the dentate gyrus was evaluated by counting the number of BrdU-positive and BrdU/NeuN double-positive cells in the dentate gyrus (DG). The number of positive cells was determined in every fifth section in a series of 40 nm sagittal sections throughout the DG using unbiased sterology. All BrdU-positive cells in the subgranular zone (SGZ) and granule cell layer (GCL) were counted using a fluorescent microscope (Nikon Eclipse 90i, Nikon Corporation, Japan). Double labeled cells were assessed by a confocal imaging system (D-Eclipse $C_1$, Nikon Corporation). Employing principles of unbiased stereology, the optical fractionator method was used to estimate cell counts for the DG. For each brain, at least 100 cells were counted based on coefficient of error determinations.

For quantitative analysis of the expression of synaptophysin and synapsin I in DG, every tenth section in a series of 40 nm coronal sections throughout the hippocampus was analyzed. The entire area of GCL was outlined. Maximum projection images were then generated based on confocal z-stacks, and antibody staining was quantified by measuring the mean optical density (OD) with the help of NIH Image J program, version 1.32j (http://rsb.info.nih.gov).

To investigate the molecular mechanism of action of compound P21 in LIF signaling, HepG2 human hepatoma cell (ATCC, USA) at 80% confluence were treated with different concentrations of P21 and with 0.25 nM LIF (Peprotec, Inc., USA) for 15 min. The cells were lysed and subjected to Western blots developed with antibodies anti-phospho-Tyr 705 STAT3 and anti-STAT3 (Cell signaling Technology, USA).

All statistical analyses were performed with STATISTICA 6.0 (StatSoft, Inc. Tulsa, USA). Data are represented as mean±SEM. ANOVAs with post hoc Fisher LSD test were used for data analyses, except data from STAT3 phosphorylation, which were analyzed by Student's t-tests. Differences with $p<0.05$ were considered significant.

Administration of the full-length CNTF protein in human clinical trials is known to cause anorexia, skeletal muscle loss, hyperalgesia, cramps, and muscle pain. However, in the present example, no alteration in either general physical state, body weight, as seen in FIG. 11($a$), exploratory behavior, as seen in FIG. 11($c$), or swim speed, as seen in FIG. 11($d$), during the period of the study could be observed, suggesting that treatment with compound P21 or P22 did not induce any apparent side effects. In the water maze task, no floating behavior was observed suggesting that animals treated with P21 or P22 did not present any sign of depression or locomotor impairment. The only general behavioral characteristic P21 and P22 altered was the level of anxiety of the mice. As shown in FIG. 11($b$), mice treated with P21 or P22 spent more time in the center of the open field than control animals ($p<0.010$, Student's t-test) suggesting lower levels of anxiety.

To examine short-term memory, a one-trial object recognition task was conducted. Mice treated with P21 clearly spent more time exploring the new object than the familiar object whereas other groups did not, as seen in FIG. 11($e$). The percentage of discrimination for animals treated with P21 was significantly increased compared to other groups, as seen in FIG. 11($f$)($p<0.05$, Student's t-test).

To investigate potential effects of P21 and P22 on hippocampal dependent memory, a spatial reference memory task in the water maze was conducted. Animals from all groups learned well, as evident by significantly declining escape latencies across training sessions, as see in FIG. 11($g$) ($p<0.05$, two-way ANOVAs). However, performance of mice treated with P21 or P22 improved significantly faster than placebotreated animals. Escape latencies to reach the submerged platform were significantly reduced for groups treated with P21 or P22 compared to control group from training day 2 to 4 ($p<0.01$, two-way ANOVA and post hoc Fisher LSD test).

To evaluate the accuracy and the strength of the platform coordinates encoding, probe trials were performed and the time animals spent looking for the platform in the target quadrant was measured. First a probe trial 24 hours after the last day of training was carried out. Then, to evaluate remote memory, probe trials 15 and 30 days after the training and the end of the chronic treatment were performed. Analysis of retention of memory in the three probe trials confirmed that all animals had correctly encoded the platform location during training since they spent more than 25% of the trial period looking for it in the target quadrant, as seen in FIG. 11($h$). During the first probe trial, animals treated with P21 focused significantly more on the target quadrant compared to control animals ($p<0.05$, Student's t-test). However, this beneficial effect disappeared on day 15 and day 30 washout periods after the end of the treatment with the peptide. No statistically significant effect of P22 was observed in the probe trials.

Overall, results from the object recognition task and the spatial reference memory task show that P21 induced positive effects on cognition.

Because neurogenesis is thought to have an important role in memory and associated learning, potential changes induced by chronic treatment with P21 and P22 were investigated.

Quantitative evaluation of neurogenesis in the DG revealed a significant increase of BrdU positive cells in the GCL and SGZ of animals treated with P21, as seen in FIGS. 12($a$) and 12($b$)($p<0.05$, two-way ANOVA and post hoc Fisher LSD test). No significant alteration in neurogenesis was observed in the group treated with P22, as seen in FIGS. 12($a$) and 12($b$).

To estimate net neurogenesis, the expression of the marker for mature neurons, NeuN, in the BrdU positive cells in the DG was examined next. A significant increase of the number of BrdU/NeuN positive cells was observed in the DG of mice treated with P21 due to a significant increased BrdU/NeuN positive cells in the GCL, as seen in FIGS. 12($a$) and 12($c$) ($p<0.05$, two-way ANOVA and post hoc Fisher LSD test). No significant changes were observed in the group of animals treated with P22.

Synapses are critical components of the neural mechanisms underlying learning and memory. In order to investigate whether P21 and P22 have neurotrophic effects, the expression of two synaptic vesicle proteins, synaptophysin and synapsin I, was measured.

Significant increases of synaptophysin and synapsin I immunoreactivities were observed in the GCL and molecular cell layer (MCL) of animals treated with P21, as seen in FIGS. 13($a$) and 13($b$)($p<0.001$, two-ways ANOVAs and post hoc Fisher LSD test). Animals treated with P22 expressed similar levels of immunoreactivity of synaptophysin and synapsin I as did untreated control animals.

To investigate whether P21 affects LIF signaling pathway, HepG2 cells were treated with different concentrations of P21 from 0.01 to 1000 nM along with 0.25 nM LIF for 15 min, and then measured STAT3 phosphorylation by Western blots. It could be observed that LIF-induced STAT3 phosphorylation was inhibited slightly in a dose-dependent manner. In HepG2 cells, 10 nM of P21 inhibited ~30% of LIFinduced phosphorylation of STAT3, as seen in FIG. 14 ($p<0.005$, Student's t-test).

Neurotrophic factors are critical for neuronal differentiation, maturation, and survival, but in the AD brain, the balance of neurotrophic factors is disturbed. Levels of basic fibroblast growth factor are upregulated, whereas the levels of brain-derived neurotrophic factor and neurotrophin 4 are reduced in the hippocampus, the frontal cortex and the parietal cortex. Because they are crucial to maintain a healthy neuronal microenvironment, neurotrophins generated excitement over the past decades as therapeutic targets for AD and other dementias. However, inconvenient pharmacokinetics and adverse side-effect profiles have limited clinical utilization of neurotrophic factors. Therefore, chemically modified short peptides able to mimic positive characteristics of neurotrophic factors represent an opportunity to circumvent these obstacles.

Derivatives of the diamondoid $C_{10}H_{16}$, hydrocarbon adamantane have already been commercialized as antivirals (amantadine, rimantadine) and as central nervous system active drugs. Nowadays, the aminoadamantane MEMANTINE® is the only drug prescribed for moderate to severe cases of AD. Based on the physicochemical and pharmacological properties of drugs incorporating the adamantane motif, an adamantane-based moiety has been used as a drug carrier for poorly absorbed compounds, including peptides, active towards the central nervous system. The foregoing examples demonstrated the beneficial effect of a CNTF based tetrapeptide, Peptide 6c, on hippocampus-dependent memory in normal adult mice. The addition of lipophilic groups to peptide 6c could increase its biostability and blood-brain-barrier permeability and consequently enhance its neurotrophic, neuroplastic, and cognitive enhancement activities. The rigid, bulky, and highly lipophilic, unnatural 3-aminoadamantane-1-carboxylic acid ("$^A$Gly") was attached C-terminally to peptide 6c to produce compound P21. The rigidity of the y-amino acid AGly should block the carboxypeptidase activity, thereby stabilizing peptide 6c in vivo. Enhancing the overall lipophilicity of peptide 6c should boost its ability to cross the BBB. Capping the N-terminus of the sequence of peptide 6c with adamantane-1-carboxylic acid in P22, would further increase lipophilicity and BBB penetration as well as resistance against aminopeptidase activity.

In AD, the hippocampus is the most vulnerable brain region to neurodegeneration. Moreover, hippocampus-dependent cognitive impairments are associated with synaptic loss which occurs early in the development of AD. Reduction of synaptophysin in the hippocampus correlates with cognitive decline in AD patients and with decreased synaptic activity in several mouse models of AD. Therefore, in the present example the effects of compounds P21 and P22 on hippocampus-dependent cognitive functions and on hippocampal synaptic plasticity were investigated.

In the present study, P21 significantly enhanced two different cognitive mechanisms; an object recognition task and a spatial reference memory task. The one-trial object recognition task is thought to critically depend on the entorhinal cortex, hippocampus and frontal cortex. In the present example it was observed that control animals as well as animals treated with P22 did not preferentially explore the novel object. This null preference did not reflect a lack of interest for novelty but rather enhanced attraction for familiarity. This reveals that, for control and P22-treated animals, familiar object representation is yet to be built and finalized, therefore requiring as much attention as the novel object to complete the encoding. On the contrary, animals treated with P21 displayed a marked preference for the novel object. This suggests that the representation of the familiar object has been fully encoded, and then was not anymore a subject of attention at the expense of the novel stimulus. These results showed that P21 treatment accelerates the encoding of object representation, thus, in the present experimental condition, improved short-term memory performance.

In the spatial reference memory task, the hippocampal system processes information about the relationships among distal environmental cues into a spatial map where spatial coordinates of the submerged platform are encoded. The hippocampus is also crucial for memory storage, consolidation and restitution of the spatial information. In the present example, it was observed that both P21 and P22 increased the learning of the task suggesting that both peptides strengthen processing of the spatial environment. However, only P21 positively enhanced performances in the probe trial. This shows that the beneficial effect of P21 on encoding, storage, and consolidation of the spatial information during the treatment period is stronger than of P22.

Examining hippocampal synaptic activity, it was found that P21 induced significant increase in synaptophysin and synapsin I immunoreactivity in the DG. Synaptophysin is a glycoprotein of the presynaptic vesicles involved in the vesicle trafficking machinery by regulating synaptic vesicle exocytosis. Besides, Synapsin I is a neuro-specific phosphoprotein highly concentrated in presynaptic nerve terminals, where, associated with the cytoplasmic surface of the synaptic vesicle, it plays a key role in neurotransmitter release. It was observed that P21 positively enhanced synaptophysin and synapsin levels. This suggests that P21 had a beneficial effect on synaptic plasticity by increasing the presynaptic release of neurotransmitters. This augmentation of neurotransmitters in the synaptic cleft may potentiate post-synaptic excitability, subsequently enhancing the efficacy of the neuronal network taking charge of stimulus processing to encode, store or recall information.

The contribution of adult hippocampal neurogenesis to memory has been studied at experimental and theoretical levels. Current literature supports the idea that both neural stem cells and immature neurons play distinct roles in hippocampus dependent memory tasks. Newly born mature cells may have an inherent advantage of being recruited into patterns of new memory networks. In the present example, it was observed that P21 increased progenitor cell proliferation as well as neuronal differentiation. Thus, through this neurogenic activity, P21 enhanced the stock of functional neurons to be potentially recruited into neuronal networks of information processing. This characteristic of P21 might be crucial as a potential treatment for neurodegeneration since in AD, although proliferation of immature neurons is increased, newly generated neurons in the DG do not mature.

The present example shows that P21 induces neuronal plasticity and neurogenic properties which consequently enhance cognition. In particular, the effects of P21 in the hippocampus were investigated, but, considering positive enhancement of the object recognition task which involves other brain structures as well as the hippocampus, it is speculated that the beneficial effect of P21 shown to be connected with neuronal plasticity in the DG may occur in other brain areas as well.

In the aforementioned examples it could be shown that peptide 6 contains a putative leukemia inhibitory factor receptor (LIFR)-binding sequence of CNTF and interferes with the signal transduction of LIF more than with that of CNTF. Because LIF inhibits neurogenesis in the DG, it was hypothesized that peptide 6 enhances neurogenesis through the CNTF pathway, inducing a partial inhibition of LIF. The present example shows that P21 acts as its parent molecule, the 11-mer peptide, partially inhibiting LIF activity through the STAT3 pathway. Because no conclusive effects of the closely related derivative P22 were observed, which differs in the N-terminal acylation, on cognition, neuronal plasticity and neurogenesis, it is assumed that incorporating an additional adamantane moeity instead of the smaller N-acetyl group at the N-terminus of P21 to furnish P22, probably prevented a proper interaction of the active-DGGL-subsequence with its receptors.

Overall, in the present example it could be shown that the CNTF-derived peptidergic compound, P21, incorporating a γ-aminoadamantane-1-carboxylic acid at its C-terminus, is neurogenic and neuroplastic and enhances cognition in normal adult mice. It is important to note that demonstrating positive effects of the studied peptides is a challenging task because it is difficult to observe enhancement of cognition due to ceiling effects in normal adult mice which were used previously. The lipophillically modified, CNTF-derived pentamer P21 is an attractive candidate for the development of pro-cognitive drugs to prevent and treat learning and memory disorders and neurodegenerative diseases such as AD and Down syndrome.

What is claimed is:

1. A method of treating a subject having Down syndrome comprising the step of administering a therapeutic amount of a neurotrophic peptide consisting of the amino acid sequence selected from the group consisting of VGDGGLFEKKL (SEQ ID NO: 1), GDGGLFEK (SEQ ID NO: 5), GLFEKKLW (SEQ ID NO: 6), VGDG (SEQ ID NO: 7), GDGG (SEQ ID NO: 8), DGGL (SEQ ID NO: 9), and GGLF (SEQ ID NO: 10).

2. The method of claim 1, wherein said neurotrophic peptide is administered subcutaneously.

3. A method of treating a subject having Down syndrome comprising the step of administering a therapeutic amount of a neurotrophic peptide consisting of the amino acid sequence DGGL (SEQ ID NO: 9) bound to an adamantane building block.

4. The method of claim 3, wherein said adamantane building block is bound to a C-terminus of said neurotrophic peptide.

5. The method of claim 3, wherein another adamantane building block is bound to an N-terminus of said neurotrophic peptide.

6. The method of claim 3, wherein said adamantane building block comprises 3-aminoadamantane-1-carboxylic acid.

7. The method of claim 3, wherein said neurotrophic peptide bound to said adamantane building block consists of the sequence Ac-DGGL$^A$G-NH$_2$ (SEQ ID NO: 12).

8. The method of claim 3, wherein said neurotrophic peptide bound to said adamantane building block consists of the sequence Ad-CO-DGGL$^A$G-NH$_2$ (SEQ ID NO: 13).

* * * * *

```
                         SEQUENCE LISTING

<160> NUMBER OF SEQ ID NOS: 15

<210> SEQ ID NO 1
<211> LENGTH: 11
<212> TYPE: PRT
<213> ORGANISM: Artificial Sequence
<220> FEATURE:
<223> OTHER INFORMATION: neurotrophic and/or neurogenic peptide

<400> SEQUENCE: 1

Val Gly Asp Gly Gly Leu Phe Glu Lys Lys Leu
1               5                   10

<210> SEQ ID NO 2
<211> LENGTH: 12
<212> TYPE: PRT
<213> ORGANISM: Artificial Sequence
<220> FEATURE:
<223> OTHER INFORMATION: neurotrophic and/or neurogenic peptide

<400> SEQUENCE: 2

Glu Asp Gln Gln Val His Phe Thr Pro Thr Glu Gly
1               5                   10

<210> SEQ ID NO 3
<211> LENGTH: 13
<212> TYPE: PRT
<213> ORGANISM: Artificial Sequence
<220> FEATURE:
<223> OTHER INFORMATION: neurotrophic and/or neurogenic peptide

<400> SEQUENCE: 3

Ile Pro Glu Asn Glu Ala Asp Gly Met Pro Ala Thr Val
1               5                   10

<210> SEQ ID NO 4
<211> LENGTH: 13
<212> TYPE: PRT
<213> ORGANISM: Artificial Sequence
<220> FEATURE:
<223> OTHER INFORMATION: neurotrophic and/or neurogenic peptide

<400> SEQUENCE: 4

Ile Pro Arg Asn Glu Ala Asp Gly Met Pro Ile Asn Val
1               5                   10

<210> SEQ ID NO 5
<211> LENGTH: 8
<212> TYPE: PRT
<213> ORGANISM: Artificial Sequence
<220> FEATURE:
<223> OTHER INFORMATION: neurotrophic and/or neurogenic peptide

<400> SEQUENCE: 5

Gly Asp Gly Gly Leu Phe Glu Lys
1               5

<210> SEQ ID NO 6
```

```
<211> LENGTH: 8
<212> TYPE: PRT
<213> ORGANISM: Artificial Sequence
<220> FEATURE:
<223> OTHER INFORMATION: neurotrophic and/or neurogenic peptide

<400> SEQUENCE: 6

Gly Leu Phe Glu Lys Lys Leu Trp
1               5

<210> SEQ ID NO 7
<211> LENGTH: 4
<212> TYPE: PRT
<213> ORGANISM: Artificial Sequence
<220> FEATURE:
<223> OTHER INFORMATION: neurotrophic and/or neurogenic peptide

<400> SEQUENCE: 7

Val Gly Asp Gly
1

<210> SEQ ID NO 8
<211> LENGTH: 4
<212> TYPE: PRT
<213> ORGANISM: Artificial Sequence
<220> FEATURE:
<223> OTHER INFORMATION: neurotrophic and/or neurogenic peptide

<400> SEQUENCE: 8

Gly Asp Gly Gly
1

<210> SEQ ID NO 9
<211> LENGTH: 4
<212> TYPE: PRT
<213> ORGANISM: Artificial Sequence
<220> FEATURE:
<223> OTHER INFORMATION: neurotrophic and/or neurogenic peptide

<400> SEQUENCE: 9

Asp Gly Gly Leu
1

<210> SEQ ID NO 10
<211> LENGTH: 4
<212> TYPE: PRT
<213> ORGANISM: Artificial Sequence
<220> FEATURE:
<223> OTHER INFORMATION: neurotrophic and/or neurogenic peptide

<400> SEQUENCE: 10

Gly Gly Leu Phe
1

<210> SEQ ID NO 11
<211> LENGTH: 11
<212> TYPE: PRT
<213> ORGANISM: Artificial Sequence
<220> FEATURE:
<223> OTHER INFORMATION: neurotrophic and/or neurogenic peptide

<400> SEQUENCE: 11

Cys His Gln Gly Cys Gly Gly Leu Phe Glu Cys
1               5                   10

<210> SEQ ID NO 12
<211> LENGTH: 4
```

```
<212> TYPE: PRT
<213> ORGANISM: Artificial Sequence
<220> FEATURE:
<223> OTHER INFORMATION: exemplified with adamantyl-L-glycine

<400> SEQUENCE: 12

Asp Gly Gly Leu
1

<210> SEQ ID NO 13
<211> LENGTH: 4
<212> TYPE: PRT
<213> ORGANISM: Artificial Sequence
<220> FEATURE:
<223> OTHER INFORMATION: exemplified with adamantyl-L-glycine

<400> SEQUENCE: 13

Asp Gly Gly Leu
1

<210> SEQ ID NO 14
<211> LENGTH: 4
<212> TYPE: PRT
<213> ORGANISM: Artificial Sequence
<220> FEATURE:
<223> OTHER INFORMATION: Xaa at position 1 represents Glu or Asp, Xaa at
      position 2 represents any amino acid, Xaa at position 3 represents
      any amino acid and Xaa at position 4 represents Glu or Asp
<220> FEATURE:
<221> NAME/KEY: misc_feature
<222> LOCATION: (1)..(4)
<223> OTHER INFORMATION: Xaa can be any naturally occurring amino acid

<400> SEQUENCE: 14

Xaa Xaa Xaa Xaa
1

<210> SEQ ID NO 15
<211> LENGTH: 8
<212> TYPE: PRT
<213> ORGANISM: Artificial Sequence
<220> FEATURE:
<223> OTHER INFORMATION: neurotrophic and/or neurogenic peptide

<400> SEQUENCE: 15

Gly Gly Leu Phe Glu Lys Lys Leu
1               5
```